(12) United States Patent
Rex et al.

(10) Patent No.: US 9,732,132 B2
(45) Date of Patent: Aug. 15, 2017

(54) THERAPEUTIC COMPOSITIONS AND METHODS FOR DISORDERS ASSOCIATED WITH NEURONAL DEGENERATION

(75) Inventors: Tonia S. Rex, Goodlettsville, TN (US); Timothy A. Sullivan, Savannah, GA (US)

(73) Assignee: Vanderbilt University, Nashville, TN (US)

( * ) Notice: Subject to any disclaimer, the term of this patent is extended or adjusted under 35 U.S.C. 154(b) by 120 days.

(21) Appl. No.: 13/979,451

(22) PCT Filed: Jan. 13, 2012

(86) PCT No.: PCT/US2012/021247
§ 371 (c)(1),
(2), (4) Date: Sep. 19, 2013

(87) PCT Pub. No.: WO2012/097256
PCT Pub. Date: Jul. 19, 2012

(65) Prior Publication Data
US 2014/0005109 A1 Jan. 2, 2014

Related U.S. Application Data

(60) Provisional application No. 61/433,186, filed on Jan. 14, 2011, provisional application No. 61/441,512, filed on Feb. 10, 2011.

(51) Int. Cl.
| | | |
|---|---|---|
| *C12N 5/00* | (2006.01) | |
| *C12N 7/00* | (2006.01) | |
| *C12N 15/09* | (2006.01) | |
| *C12N 15/18* | (2006.01) | |
| *C07K 14/505* | (2006.01) | |
| *C12N 15/00* | (2006.01) | |
| *C12N 15/86* | (2006.01) | |
| *C12N 15/10* | (2006.01) | |

(52) U.S. Cl.
CPC ............. *C07K 14/505* (2013.01); *C12N 5/00* (2013.01); *C12N 7/00* (2013.01); *C12N 15/00* (2013.01); *C12N 15/10* (2013.01); *C12N 15/86* (2013.01)

(58) Field of Classification Search
None
See application file for complete search history.

(56) References Cited

U.S. PATENT DOCUMENTS

| | | | | |
|---|---|---|---|---|
| 4,677,195 A * | 6/1987 | Hewick | ................ | C07K 14/505 514/20.9 |
| 5,846,528 A * | 12/1998 | Podsakoff et al. | ........... | 424/93.2 |
| 7,067,477 B2 * | 6/2006 | MacLeod | ....................... | 514/7.7 |
| 8,252,743 B2 * | 8/2012 | Guyon et al. | .................. | 514/7.7 |
| 2004/0122216 A1 * | 6/2004 | Nielsen et al. | ............... | 530/351 |
| 2004/0132977 A1 * | 7/2004 | Gantier et al. | ................ | 530/351 |
| 2006/0204473 A1 | 9/2006 | Blatt et al. | | |
| 2007/0100133 A1 * | 5/2007 | Beals | ................ | A61K 38/1816 530/350 |
| 2008/0260746 A1 * | 10/2008 | Abderrahim et al. | ..... | 424/139.1 |
| 2009/0238789 A1 | 9/2009 | Guyon et al. | | |
| 2010/0093608 A1 | 4/2010 | Tian et al. | | |

FOREIGN PATENT DOCUMENTS

WO    WO-03-055526 A2 *    7/2003

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Colella et al. AAV-Mediated Gene Supply of Non-Erythropoietic Erythropoietin Derivatives Improves Photoreceptor Morphology and Function in Models of Retinal Degenerative Diseases. Abstract 443, p. S172. Molecular Therapy vol. 18, Supplement 1, (May 2010).*
Colella et al. Gene Transfer of Erythropoietin derivatives protects from photoreceptor degeneration. Abstract Or 111, p. 1394. Human Gene Therapy vol. 21(Oct. 2010).*
Leist et al. Derivatives of Erythropoietin that are tissue protective but not erythropoietic. Science 305:239-242 (2004).*
Sullivan et al., "Systemic Adeno-associated Virus-Mediated Gene Therapy Preserves Retinal Ganglion Cells and Visual Function n DBA/2J Glaucomatous Mice," Hum Gene Ther., 2011, 10:1191-200.

(Continued)

*Primary Examiner* — Elizabeth C Kemmerer
*Assistant Examiner* — Regina M Deberry
(74) *Attorney, Agent, or Firm* — Stites & Harbison PLLC; Mandy Wilson Decker

(57) ABSTRACT

Disclosed are isolated mutant erythropoietin (EPO) polypeptides, functional fragment thereof, nucleic acid encoding such peptides, vectors including such nucleic acids and compositions including such peptides and nucleic acids. The mutant EPO peptides are unique in that they include a substitution at amino acid position number 76, such as a glutamic acid for arginine substitution at position 76. This substitution inhibits erythropoietic activity while retaining their neuroprotection. Also disclosed are methods of treating or inhibiting neuronal degeneration, reducing or inhibiting one or more symptoms associated with neuronal degeneration and/or glaucoma in a subject. The methods include administering a therapeutically effective amount of a isolated mutant erythropoietin EPO polypeptide, an expression vector encoding such a mutant erythropoietin EPO polypeptide, a viral particle including an expression vector, or a composition, thereby treating or inhibiting neuronal degeneration in the subject.

11 Claims, 16 Drawing Sheets

(56) References Cited

OTHER PUBLICATIONS

Sullivan et al., "Systemic Gene Delivery Protects the Photoreceptors in the Retinal Degeneration Slow Mouse," Neurochem Res., 2011, 36:613-618.
International Search Report and Written Opinion, issued Apr. 26, 2012 by the United States Patent Office for corresponding PCT Patent Application No. PCT/US2012/0321247, 9 pp.

* cited by examiner

SEQUENCE LISTING

```
<160> NUMBER OF SEQ ID NOS: 13

<210> SEQ ID NO 1
<211> LENGTH: 166
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
```

```
<222> LOCATION: (76)..(76)
<223> OTHER INFORMATION: X at position 76 is any amino acid except ARG

<400> SEQUENCE: 1

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Xaa Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 2
<211> LENGTH: 166
<212> TYPE: PRT
<213> ORGANISM: Artificial Sequence
<220> FEATURE:
<223> OTHER INFORMATION: Synthetic peptide construct

<400> SEQUENCE: 2

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Glu Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
```

-continued

```
<210> SEQ ID NO 3
<211> LENGTH: 166
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (76)..(76)
<223> OTHER INFORMATION: X is any amino acid except ARG
<220> FEATURE:
<221> NAME/KEY: MISC_FEATURE
<222> LOCATION: (100)..(100)
<223> OTHER INFORMATION: X is any amino acid except SER
<220> FEATURE:
<221> NAME/KEY: MISC_FEATURE
<222> LOCATION: (103)..(103)
<223> OTHER INFORMATION: X is any amino acid except ARG

<400> SEQUENCE: 3

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Xaa Gly Gln Ala Leu
65                  70                  75                  80

Leu Val Asn Ser Ser Gln Pro Trp Glu Pro Leu Gln Leu His Val Asp
                85                  90                  95

Lys Ala Val Xaa Gly Leu Xaa Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 4
<211> LENGTH: 27
<212> TYPE: PRT
<213> ORGANISM: Artificial Sequence
<220> FEATURE:
<223> OTHER INFORMATION: Synthetic peptide construct

<400> SEQUENCE: 4

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 5
<211> LENGTH: 193
<212> TYPE: PRT
<213> ORGANISM: Artificial Sequence
<220> FEATURE:
```

<223> OTHER INFORMATION: Synthetic peptide construct
<220> FEATURE:
<221> NAME/KEY: MISC_FEATURE
<222> LOCATION: (103)..(103)
<223> OTHER INFORMATION: X is any amino acid except ARG

<400> SEQUENCE: 5

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Xaa Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 6
<211> LENGTH: 193
<212> TYPE: PRT
<213> ORGANISM: Artificial Sequence
<220> FEATURE:
<223> OTHER INFORMATION: Synthetic peptide construct

<400> SEQUENCE: 6

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Glu Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

```
Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 7
<211> LENGTH: 193
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (103)..(103)
<223> OTHER INFORMATION: X is Glutamic Acid
<220> FEATURE:
<221> NAME/KEY: MISC_FEATURE
<222> LOCATION: (127)..(127)
<223> OTHER INFORMATION: X is any amino acid except SER
<220> FEATURE:
<221> NAME/KEY: MISC_FEATURE
<222> LOCATION: (130)..(130)
<223> OTHER INFORMATION: X is any amino acid except ARG

<400> SEQUENCE: 7

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Xaa Gly Gln Ala Leu Leu Val Asn Ser Ser
            100                 105                 110

Gln Pro Trp Glu Pro Leu Gln Leu His Val Asp Lys Ala Val Xaa Gly
        115                 120                 125

Leu Xaa Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 8
<211> LENGTH: 193
<212> TYPE: PRT
```

<213> ORGANISM: Artificial Sequence
<220> FEATURE:
<223> OTHER INFORMATION: Synthetic peptide construct

<400> SEQUENCE: 8

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
50                  55                      60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Glu Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg
```

<210> SEQ ID NO 9
<211> LENGTH: 579
<212> TYPE: DNA
<213> ORGANISM: Artificial Sequence
<220> FEATURE:
<223> OTHER INFORMATION: Synthetic oligonucleotide construct

<400> SEQUENCE: 9

```
atgggggtgc acgaatgtcc tgcctggctg tggcttctcc tgtctctgct ctcgctccct    60
ctgggcctcc cagtcccggg cgccccacca cgcctcatct gtgacagccg agtcctggag   120
aggtacctct tggaggccaa ggaggccgag aatgtcacga tgggctgttc cgaaagctgc   180
agcttgaatg agaatatcac cgtcccagac accaaagtta acttctatgc ctggaagagg   240
atggaggtcg ggcagcaggc tgtagaagtc tggcagggcc tggccctgct ctcagaagct   300
gtcctggagg ccaggccgt gttggccaac tcttcccagc ctttcgagcc cctgcagctg   360
cacatggata aagccatcag tggccttcgc agcatcacca ctctgcttcg ggcgctggga   420
gcccaggaag ccatctcccct cccagatgcg gcctcggctg ctccactccg aaccatcact   480
gctgacactt tctgcaaact cttccgagtc tactccaatt cctccgggg aaagctgaag   540
ctgtacacgg gggaggcctg caggagaggg gacagatga               579
```

<210> SEQ ID NO 10
<211> LENGTH: 29
<212> TYPE: DNA
<213> ORGANISM: Artificial Sequence

```
<220> FEATURE:
<223> OTHER INFORMATION: Synthetic oligonucleotide primer

<400> SEQUENCE: 10
ctcagaagct gtcctggagg gccaggccg                              29

<210> SEQ ID NO 11
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 11
gggcctggcc ctgctcgaag aagctgtcc                              29

<210> SEQ ID NO 12
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 12
gtcatatgcg gccgcatggg ggtgcacgaa tg                          32

<210> SEQ ID NO 13
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 13
gatccaagct ttcatctgtc ccctctcctg ca                          32
```

THERAPEUTIC COMPOSITIONS AND METHODS FOR DISORDERS ASSOCIATED WITH NEURONAL DEGENERATION

CROSS REFERENCE TO RELATED APPLICATIONS

This is the U.S. National Stage of International Application No. PCT/US2012/021247, filed Jan. 13, 2012, published in English under PCT Article 21 (2), which claims the benefit of U.S. Provisional Application No. 61/433,186, filed Jan. 14, 2011, and U.S. Provisional Application No. 61/441,512, filed Feb. 10, 2011. Both of these provisional applications are specifically incorporated by reference herein in their entirety.

STATEMENT OF GOVERNMENT INTEREST

This invention was made with government support under contract numbers 5P30EY13080, R01EY017841, awarded by the National Institutes of Health, and W81XWH-10-1-0528, awarded by the U.S. Army Medical Research and Materiel Command, the Telemedicine & Advanced Technology Research Center. The government has certain rights in the invention.

FIELD OF THE DISCLOSURE

The present disclosure relates to compositions and methods for the treatment of disorders associated with neuronal degeneration. More specifically, the present disclosure relates to of a mutant form of erythropoietin (EPO) for the treatment of disorders associated with neuronal degeneration.

BACKGROUND

Glaucoma refers to a group of eye conditions that lead to damage to the optic nerve (the nerve that carries visual information from the eye to the brain). In many cases, damage to the optic nerve is due to increased pressure in the eye, also known as intraocular pressure (IOP). Glaucoma is the second most common cause of blindness in the United States. There are three major types of glaucoma: open-angle glaucoma or chronic glaucoma, congenital glaucoma, and angle closure (acute) glaucoma.

The front part of the eye is filled with a clear fluid called aqueous humor that is produced by the ciliary body, which forms a barrier between the anterior and posterior chambers of the eye. This fluid leaves the eye through channels in the front of the eye in an area called the anterior chamber angle, or simply the angle. Anything that slows or blocks the flow of this fluid out of the eye will cause pressure to build up in the eye. This pressure is called intraocular pressure (IOP). In most cases of glaucoma, this pressure is high and causes damage to the optic nerve, the major nerve in the eye.

Open-angle (chronic) glaucoma is the most common type of glaucoma, but its cause is unknown. An increase in eye pressure occurs slowly over time. The pressure pushes on the optic nerve and the retina at the back of the eye. Open-angle glaucoma tends to run in families. The risk is higher if a patient has a parent or grandparent with open-angle glaucoma, and people of African descent are at particularly high risk for this disease. Most people have no symptoms until they begin to lose vision and then experience gradual loss of peripheral (side) vision (also called tunnel vision).

Angle-closure (acute) glaucoma occurs when the exit of the aqueous humor fluid is suddenly blocked. This causes a quick, severe, and painful rise in the pressure within the eye (intraocular pressure). Angle-closure glaucoma is an emergency. This is very different from open-angle glaucoma, which painlessly and slowly damages vision. Symptoms of angle-closure glaucoma may come and go at first, or steadily become worse and may develop into sudden, severe pain in one eye, decreased or cloudy vision, nausea and vomiting, rainbow-like halos around lights, red eye, and a swollen sensation in the eye.

Congenital glaucoma often is hereditary and results from the abnormal development of the fluid outflow channels in the eye. The symptoms are usually noticed when the child is a few months old and they include cloudiness of the front of the eye, enlargement of one eye or both eyes, red eye, sensitivity to light, and tearing.

An eye exam may be used to diagnose glaucoma. The physician will need to examine the inside of the eye by looking through the pupil, often while the pupil is dilated. The physician will usually perform a complete eye exam. Checking the intraocular pressure alone (tonometry) is not enough to diagnose glaucoma because eye pressure changes. Pressure in the eye is normal in about 25% of people with glaucoma. This is called normal-tension glaucoma. There are also other problems that cause optic nerve damage, thus necessitating a complete eye exam.

Tests to diagnose glaucoma include: gonioscopy (use of a special lens to see the outflow channels of the angle), tonometry test to measure eye pressure, optic nerve imaging (photographs of the inside of the eye), pupillary reflex response, retinal examination, slit lamp examination, visual acuity, and visual field measurement.

Although some forms of glaucoma treatment are available, none are adequate. Thus, there remains a need for a therapeutic regimen that is easy to administer, has minimal or no side effects, and that has long lasting efficacy. The goal of current treatment is to reduce eye pressure. Depending on the type of glaucoma, this is currently done using medications or surgery. Most people with open-angle glaucoma can be treated with some degree of success with these pressure lowering eye drops. However, most eye drops used today continue to have unpredictable side effects. Many times, more than one type of drop may be necessary. Some patients may also be treated with pills to lower pressure in the eye. Improved eye drops and pills that may protect the optic nerve from glaucoma damage are desirable. Some patients need other forms of treatment, such as laser treatment, to help open the fluid outflow channels. This procedure is usually painless. Others may need traditional surgery to open a new outflow channel.

Angle-closure glaucoma treatment requires immediate medical intervention. Acute angle-closure attack is a medical emergency and blindness will occur in as little as a few days if the closure is not treated. Drops, pills, and medicine given through a vein (by IV) are used to lower pressure. Some people also need an emergency operation, called an iridotomy. This procedure uses a laser to open a new channel in the iris. The new channel relieves pressure and prevents another attack. But, this procedure is not without the risk of side effects, which include a transient increased IOP, inflammation within the eye, damage to the corneal epithelium, opacification of the cornea, bleeding of the iris, and macular edema. Some patients also experience glare and double vision after the procedure, and there may also be a transient blurry vision.

As for congenital glaucoma, treatment almost always requires surgery to open the outflow channels of the angle. This is done while the patient is under anesthesia so that the patient feels no pain during the procedure. But like any surgery, side affects such as post-operative pain and infection may occur.

An alternative strategy is to block cell death by a gene independent approach, such as treatment with neuroprotective therapy. Gene delivery of erythropoietin (EPO) overcomes two major challenges associated with neuroprotective therapy. First, virus mediated gene delivery provides long term gene expression, overcoming the need for repeat delivery because of the short half-life of most neuroprotective agents. Second, EPO, unlike other neuroprotective proteins, is able to cross the blood retina and blood brain barrier. One major problem associated with the administration of EPO, however, is a rise in hematocrit levels.

What are needed are improved and effective compositions and methods for the treatment of disorders associated with retinal degeneration, such as glaucoma, that are independent of intraocular pressure. More specifically, what are needed are compositions and methods for systemic delivery of therapeutic agents having quick and long lasting effects and minimal side effects.

SUMMARY OF THE DISCLOSURE

Disclosed are isolated mutant erythropoietin (EPO) polypeptides, functional fragment thereof, nucleic acid encoding such peptides, vectors including such nucleic acids, and compositions including such polypeptides and nucleic acid. The disclosed mutant EPO peptides are unique in that they include a substitution at amino acid position number 76, such as a glutamic acid for arginine substitution at position 76. This substitution renders the resulting peptides non-erythropoietic while retaining their neuroprotective properties. In some examples, the mutant EPO polypeptide further includes an additional mutation at one or both of amino acid positions 100, and/or 103, such as a substitution of glutamic acid for serine at position 100 and/or a substitution of glutamic acid for arginine at position number 103. In some examples, the isolated mutant erythropoietin EPO polypeptide comprises or consists essentially of amino acid residues 28-193 of EPO. In some examples, the isolated mutant erythropoietin EPO polypeptide comprises or consists essentially of amino acid residues 1-193 of EPO. In specific examples, the isolated mutant erythropoietin EPO polypeptide comprises or consists essentially of the amino acid sequence set forth as any one of SEQ ID NOs: 1-3 or 5-8 or functional fragment thereof.

Also disclosed are nucleic acids encoding the mutant EPO polypeptides. In a particular example, an isolated nucleic acid molecule encoding the isolated mutant erythropoietin EPO polypeptide includes the nucleic acid sequences set forth as SEQ ID NO: 9. Expression vectors, such as mammalian expression vectors, including such nucleic acids are disclosed. In some examples, the mammalian expression vector is a viral expression vector. In specific examples, the viral expression vector is an adeno-associated virus (AAV) vector. A viral particle including an expression vector is disclosed.

Also disclosed are methods of treating or inhibiting neuronal degeneration and reducing or inhibiting one or more symptoms associated with neuronal degeneration, in a subject. The methods include administering to the subject a therapeutically effective amount of a isolated mutant erythropoietin EPO polypeptide, a nucleic acid encoding such a mutant erythropoietin EPO polypeptide, an expression vector including such a nucleic acid, a viral particle including an expression vector, or a composition including any of the above, thereby treating or inhibiting neuronal degeneration in the subject. In a specific example, the method is a method of treating glaucoma in a subject.

These and other features and advantages of the present disclosure will become apparent after a review of the following detailed description of the disclosed embodiments and the appended claims.

BRIEF DESCRIPTION OF THE FIGURES

FIG. 4A is a set of bright-field micrographs of optic nerve cross-sections (original magnification, 60x) stained with p-phenylenediamine (PPD). Nerves from preglaucomatous mice (3 months old) have a high density of healthy axons (top left, white arrow). At 10 months of age optic nerves from control mice (rAAV2/5.CMV.eGFP) had profound axonal degeneration marked by the loss of healthy axons, increased sick/dying axons (top right, solid arrows), and gliosis (top right, open arrow). The majority of optic nerves from mice that were treated with either EPO vector (bottom left and right) had little or no axonal degeneration. FIG. 4B is a bar graph of the number of healthy axons per optic nerve. Data represent means±SEM, and statistical analysis was performed by one-way analysis of variance with pairwise Bonferroni post hoc test; **$p \leq 0.001$ versus rAAV2/5.CMV.eGFP. There was no statistically significant difference between the preglaucomatous, rAAV2/5.CMV.Epo, and rAAV2/5.CMV.EpoR76E groups.

FIG. 5A is a set of digital images of confocal micrographs (original magnification, 40×) of retinal flat mounts from DBA/2J mice and labeled with anti-NeuN. The first column contains representative images from 3-month-old preglaucomatous mice. Columns 2-4 contain representative images from 10-month-old DBA/2J mice treated with rAAV2/5.CMV.eGFP, rAAV2/5.CMV.Epo, or rAAV2/5.CMV.EpoR76E, respectively. All images come from independent eyes. FIG. 5B is a bar graph showing average density of NeuN-positive cells. Data represent means±SEM, and statistical analysis was done by one-way analysis of variance with pair-wise Bonferroni post hoc test; **$p \leq 0.001$ versus rAAV2/S.CMV.eGFP. There was no statistically significant difference between the preglaucomatous, rAAV2/5.CMV.Epo, and rAAV2/5.CMV.EpoR76E groups.

FIG. 6A is a set of graphs showing the average waveforms of the flash visual evoked potential (F-VEP) in control and treated mice.

FIGS. 6B-6E is a set of bar graphs of the peak amplitudes of (FIG. 6B) N1 and (FIG. 6C) P1 waves and the latency of the (FIG. 6D) N1 and (FIG. 6E) P1 waves. Data represent means±SEM, and statistical analysis was done by one-way analysis of variance with pair-wise Bonferroni post hoc test; *$p \leq 0.01$; **$p \leq 0.001$ versus rAAV2/5.CMV.eGFP. There was no statistically significant difference in the N1 and P1 peak amplitude between the preglaucomatous control mice, the rAAV2/S.CMV.Epo-treated mice, and the rAAV2/S.CMV.EpoR76E-treated mice. There was no statistically significant difference in the peak latency of the N1 and P1 waves between any of the treatment groups and the preglaucomatous control mice. The up arrow (↑) in (FIG. 6A) indicates a flash of light.

FIG. 8A is a set of digital images of confocal micrographs of retinal flat mounts labeled with anti NeuN. Images are from the ganglion cell layer of the retina. FIG. 8B is a bar graph showing the average density of NeuN positive cells. Data are means±S.E.M., and statistical analysis was done by one-way ANOVA with pair-wise Bonferroni post hoc test. eGFP=enhanced green fluorescent protein, *$p \leq 0.05$, $p \leq 0.01$, *$p \leq 0.001$ vs. eGFP. Scale bar=50 µm.

FIG. 9A is a set of digital images of brightfield micrographs of optic nerve cross sections stained with PPD. FIG. 9B is a bar graph of average number of axons per optic nerve. There was no statistically significant difference between groups that received vector treatment. Data are means±S.E.M., and statistical analysis was performed by one-way ANOVA with pair-wise Bonferroni post hoc test. Healthy axons (white arrow), degenerating/dying axons (→) and gliosis (⇒) are indicated. Scale bar=10 µm.

FIG. 13A, Mice were placed in a force-plate actometer and allowed to explore freely for 5 min. Minute variations in force were recorded on a millisecond time scale. MPTP induced a robust 7-9-Hz tremor in control mice pre-treated with rAAV.eGFP. Mice injected with either of the modified Epo constructs did not exhibit MPTP-induced tremor. FIG. 13B, Mice in the rAAV.eGFP control group and lesioned with MPTP were slower to move all four paws when placed on a horizontal grid. Mice pretreated with rAAV.EpoS71E or rAAV.EpoR76E did not exhibit this MPTP-induced akinesia.

(FIGS. 14A and 14D) MPTP destroyed ~40% of the TH-positive neurons in the SNc in control mice pretreated with rAAV.eGFP, and induced a similar-sized lesion in the rAAV.EpoS71E group (FIGS. 14B and 14E). (FIGS. 14C and 14F) Mice pretreated with rAAV.EpoR76E were partially protected against the MPTP lesion, exhibiting a ~20% loss of TH-positive SNc cells. (FIG. 14G) Stereological quantification of the images presented in FIGS. 14A-14F.

FIG. 15A, Intracellular striatal dopamine (DA) measured by HPLC 8 weeks following the last injection of saline or 18 mg/kg MPTP. There were no significant differences in dopamine across groups, possibly due in part to axon regeneration and sprouting of new terminals following MPTP lesion. FIG. 15B, The DA degradative enzyme DOPAC was significantly lower in MPTP-lesioned mice pretreated with rAAV.eGFP, compared to their saline-treated counterparts, suggesting reduced DA turnover. In contrast, mice pre-treated with either of the modified Epo variants had normal DOPAC regardless of lesion status.

(FIGS. 16A-16F) Density of TH-positive fibers was assessed in striatal sections 8 weeks following administration of MPTP or saline. MPTP-lesioned mice pretreated with rAAV.eGFP showed a characteristic loss of TH-positive fibers compared to saline-treated controls (FIGS. 16A and 16D). Mice pretreated with rAAV.EpoR76E showed a similar magnitude of MPTP lesion (FIGS. 16C and 16F). In contrast, mice in the rAAV.EpoS71E group exhibited no loss of TH-positive fibers after MPTP treatment, presumably due to increased axonal sprouting and regeneration (FIGS. 16B and 16E). Confocal images of striatal sections show increased density of TH-positive fibers in MPTP-lesioned mice pretreated with rAAV.eGFP (FIG. 16G) or rAAV.EpoS71E FIG. 16H. FIG. 16I, Densitometric quantification of the images presented in FIGS. 16A-16F.

SEQUENCE LISTING

Figure 1:
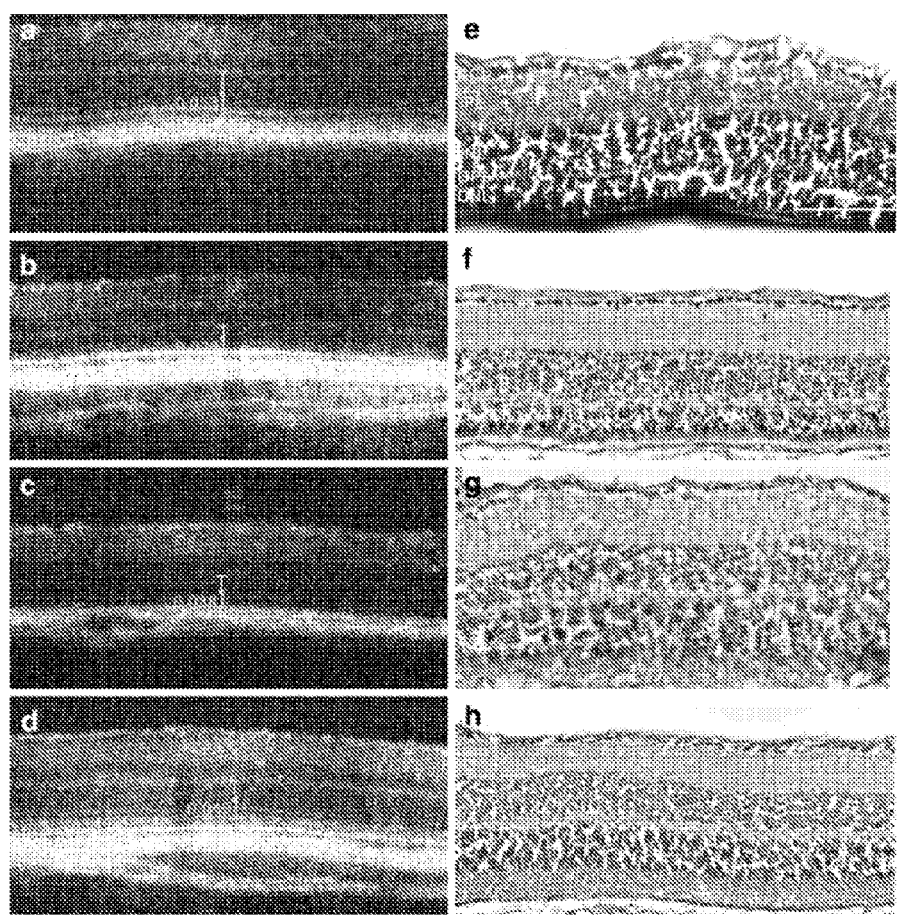
FIGS. 1A-1H are digital images of slides showing that treatment with either rAAV2/5.CMV.Epo or rAAV2/5.CMV.Epo-R76E protects photoreceptors from cell death. Optical coherence tomography (FIGS. 1A-1D) and histological cross section (FIGS. 1E-1H) images of wild-type (FIG. 1A and FIG. 1E) and rds/rds (FIGS. 1B-1D and 1F-1H) mice treated with rAAV2/5.CMV.eGFP (FIGS. 1B and 1F), rAAV2/5.CMV.Epo (FIGS. 1C and 1G), or rAAV2/5.CMV.EpoR76E (FIGS. 1D and 1H). The calipers in FIGS. 1A-1D indicate the micron thickness of the outer nuclear layer (ONL), 0.038, 0.020, 0.053, and 0.042, respectively. (GCL, ganglion cell layer. IPL, inner plexiform layer. INL, inner nuclear layer, OPL, outer plexiform layer. ONL, outer nuclear layer).

The nucleic and amino acid sequences listed in the accompanying sequence listing are shown using standard letter abbreviations for nucleotide bases, and three letter code for amino acids, as defined in 37 C.F.R. §1.822. Only one strand of each nucleic acid sequence is shown, but the complementary strand is understood as included by any reference to the displayed strand. In the accompanying sequence listing:

SEQ ID NOs: 1-3 and 5-8 are exemplary amino acid sequence of EPO polypeptides with the R76E mutation.

SEQ ID NO: 4 is the amino acid sequence of an EPO leader sequence.

SEQ ID NO: 9 is a exemplary nucleic acid sequence of EPO R76E mutant.

SEQ ID NOs: 10-13 are oligonucleotide primers.

The Sequence Listing is submitted as an ASCII text file in the form of the file named UTM-0101WP_ST25.txt, which was created on Dec. 11, 2012, and is 15 kilobytes, which is incorporated by reference herein.

DETAILED DESCRIPTION OF SEVERAL EMBODIMENTS

I. Summary of Terms

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

To facilitate review of the various embodiments of this disclosure, the following explanations of terms are provided:

Administration: The introduction of a composition into a subject by a chosen route. Administration can be local or systemic. For example, if the chosen route is intravenous, the composition is administered by introducing the composition into a vein of the subject. Similarly, if the chosen route is intramuscular, the composition is administered by introducing the composition into one or more muscles of the subject. In some examples, a disclosed erythropoietin protein or polypeptide, or nucleic acid encoding a disclosed erythropoietin protein or polypeptide, having an amino acid substitution at position 76, such as a glutamic acid for arginine substitution, at position 76 is administered to a subject.

Amino acid substitution: The replacement of one amino acid in peptide with a different amino acid. For example, the replacement of an arginine with glutamic acid at position 76 of an EPO protein or peptide.

Animal: A living multi-cellular vertebrate or invertebrate organism, a category that includes, for example, mammals. The term mammal includes both human and non-human mammals. Similarly, the term "subject" includes both human and veterinary subjects, such as non-human primates. Thus, administration to a subject can include administration to a human subject. Particular examples of veterinary subjects include domesticated animals (such as cats and dogs), livestock (for example, cattle, horses, pigs, sheep, and goats), and laboratory animals (for example, mice, rabbits, rats, gerbils, guinea pigs, and non-human primates).

Degenerate variant and conservative variant: A polynucleotide encoding a polypeptide that includes a sequence that is degenerate as a result of the genetic code. For example, a polynucleotide encoding a disclosed EPO mutant includes a sequence that is degenerate as a result of the genetic code. There are 20 natural amino acids, most of which are specified by more than one codon. Therefore, all degenerate nucleotide sequences are included as long as the amino acid sequence of the peptide or protein encoded by the nucleotide sequence is unchanged.

One of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Not all residue positions within a protein will tolerate an otherwise "conservative" substitution. For instance, if an amino acid residue is essential for a function of the protein, even an otherwise conservative substitution may disrupt that activity.

Expression: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter, the cytomegalovirus promoter) can be used. Promoters produced by recombinant DNA or synthetic techniques may also be used to provide for transcription of the nucleic acid sequences.

Erythropoietin (EPO): A glycoprotein hormone that controls erythropoiesis, or red blood cell production. It is a cytokine for erythrocyte (red blood cell) precursors in the bone marrow. It also has other known biological functions. For example, erythropoietin plays a role in the response to neuronal injury. Typically, erythropoietin is produced as a 193 residue precursor protein, with the N-terminal 27 amino acids removed through posttranslational processing of the pro-protein.

Exemplary amino acid sequences of human EPO are known in the art and can be found for example in GEN-BANK® at accession number NP_000790, as available Dec. 28, 2011, which is incorporated herein by reference in its entirety. Exemplary nucleic acid sequences of human EPO are known in the art and can be found for example in GENBANK® at accession number NM_000799, as available Dec. 28, 2011, which is incorporated herein by reference in its entirety.

Inhibiting or treating a disease: Inhibiting the full development of a disease or condition, for example, in a subject who is at risk for a disease such as neuronal degeneration, for example glucoma. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a EPO peptide, protein or nucleic acid) has been substantially separated, produced apart from, or purified away from other biological components in the cell of the organism in which the component naturally occurs, such as, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides, and proteins prepared by recombinant expression in a host cell as well as chemically synthesized nucleic acids.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid, which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the proteins, peptides and nucleic acids herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. In some examples, a pharmaceutical agent includes a mutant EPO polypeptide and/or nucleic acid.

Polypeptide: Any chain of amino acids, regardless of length or post-translational modification (e.g., glycosylation or phosphorylation). In one embodiment, the polypeptide is a mutant EPO polypeptide. A "residue" refers to an amino acid or amino acid mimetic incorporated in a polypeptide by an amide bond or amide bond mimetic. A polypeptide has an amino terminal (N-terminal) end and a carboxy terminal (C-terminal) end.

Purified: The term purified does not require absolute purity; rather, it is intended as a relative term. Thus, for example, a purified peptide preparation is one in which the peptide or protein (such as mutant EPO) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence, for example an adeno-associated virus (AAV) in which part of its genome is replaced with a heterologous gene, such as a gene encoding a mutant EPO. This artificial combination is often accomplished by chemical synthesis or, more commonly, by the artificial manipulation of isolated segments of nucleic acids, e.g., by genetic engineering techniques.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Therapeutic agent: Used in a generic sense, it includes treating agents, prophylactic agents, and replacement agents.

Therapeutically effective amount or effective amount: A quantity of a specific substance, such as a disclosed EPO mutant, sufficient to achieve a desired effect in a subject being treated. For instance, this can be the amount necessary to inhibit neuronal degeneration. In several embodiments, a therapeutically effective amount is the amount necessary to reduce a sign or symptom of glaucoma in a subject. When administered to a subject, a dosage will generally be used that will achieve target tissue concentrations that has been shown to achieve a desired in vivo effect.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. Viral vectors can be used to deliver genetic material into cells. This process can be performed inside a living organism (in vivo) or in cell culture (in vitro). Viruses have evolved specialized molecular mechanisms to efficiently transport their genomes inside the cells they infect. Several types of viruses are commonly used to transfer genetic material to a cell, for example retroviruses (such as lentivirus), adenoviruses and adeno-associated viruses.

Retroviruses such as the Moloney murine leukemia virus have the ability to integrate into the host genome in a stable fashion. They contain a reverse transcriptase that allows integration into the host genome. They have been used in a number of FDA-approved clinical trials such as the SCID-X1 trial. Retroviral vectors can either be replication-competent or replication-defective. Replication-defective vectors are the most common choice in studies because the viruses have had the coding regions for the genes necessary for additional rounds of virion replication and packaging replaced with other genes, or deleted. These virus are capable of infecting their target cells and delivering their viral payload, but then fail to continue the typical lytic pathway that leads to cell lysis and death. Conversely, replication-competent viral vectors contain all necessary genes for virion synthesis, and continue to propagate themselves once infection occurs. Because the viral genome for these vectors is much lengthier, the length of the actual inserted gene of interest is limited compared to the possible length of the insert for replication-defective vectors.

Lentiviruses are a subclass of Retroviruses. They have been adapted as gene delivery vehicles (vectors) thanks to their ability to integrate into the genome of non-dividing cells, which is the unique feature of Lentiviruses as other Retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides. Typically lentiviral vectors never carry the genes required for their replication. To produce a lentivirus, several plasmids are transfected into a so-called packaging cell line, such as HEK 293 cells. One or more plasmids, generally referred to as packaging plasmids, encode the virion proteins, such as the capsid and the reverse transcriptase. Another plasmid contains the genetic material to be delivered by the vector.

Adenoviral DNA does not integrate into the genome and is not replicated during cell division.

Adeno-associated viruses (AAV), from the parvovirus family, are small viruses with a genome of single stranded DNA. AAV is not currently known to cause disease and consequently the virus causes a very mild immune response. AAV can infect both dividing and non-dividing cells and may incorporate its genome into that of the host cell. These viruses can insert genetic material at a specific site on chromosome 19 with near 100% certainty. In contrast to adenoviruses, most people treated with AAV will not build an immune response to remove the virus and the cells that have been successfully treated with it. These features make AAV a very attractive candidate for creating viral vectors for gene delivery applications.

Several trials with AAV are on-going or in preparation, mainly trying to treat muscle and eye diseases—the two tissues where the virus seems particularly useful. However, clinical trials have also been initiated where AAV vectors are used to deliver genes to the brain. This is possible because AAV viruses can infect non-dividing (quiescent) cells, such as neurons in which their genomes are expressed for a long time.

The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry. The Inverted Terminal Repeat (ITR) sequences comprise 145 bases each. They were named so because of their symmetry, which was shown to be required for efficient multiplication of the AAV genome. Another property of these sequences is their ability to form a hairpin, which contributes to so-called self-priming that allows primase-independent synthesis of the second DNA strand. The ITRs were also shown to be required for both integration of the AAV DNA into the host cell genome and rescue from it, as well as for efficient encapsidation of the AAV DNA combined with generation of a fully-assembled, deoxyribonuclease-resistant AAV particles.

There have been multiple serotypes described. All of the known serotypes can infect cells from multiple diverse tissue types. Tissue specificity is determined by the capsid serotype and pseudotyping of AAV vectors to alter their tropism range will likely be important to their use in therapy. Serotype 2 (AAV2) has been the most extensively examined so far. AAV2 presents natural tropism towards neurons.

Although AAV2 is the most popular serotype in various AAV-based research, it has been shown that other serotypes can be more effective as gene delivery vectors. For instance AAV6 appears much better in infecting airway epithelial cells, AAV7 presents very high transduction rate of murine skeletal muscle cells (similarly to AAV1 and AAV5), AAV8 is superb in transducing hepatocytes and AAV1 and 5 were shown to be very efficient in gene delivery to vascular endothelial cells. AAV6, a hybrid of AAV1 and AAV2, also shows lower immunogenicity than AAV2.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and, Harlow and Lane, *Using Antibodies: A Laboratory Manual*, Cold Spring Harbor Laboratory Press, 1999. In addition, the materials, methods, and examples are illustrative only and not intended to be limiting.

II. Description of Several Embodiments

A. Introduction

Many neurodegenerative diseases such as Alzheimer's, amyotrophic lateral sclerosis (ALS), multiple sclerosis (MS), Parkinson's, and glaucoma are characterized by the slow, progressive loss of neurons. In most of these cases, neuronal death is triggered by a variety of factors that are disease specific. Autoimmunity plays a key role in MS causing severe axonal damage, as well as in ALS, where it leads to loss of motor neurons Alzheimer's is often associated with plaques and tangles in the brain and in glaucoma it appears that an increase in intraocular pressure (IOP) causes axonal damage and retinal ganglion cell (RGC) death. Whereas many laboratories are working to develop disease specific interventions, the goal of the studies disclosed herein was to develop general neuroprotective treatments that ameliorate neurodegenerative diseases regardless of their initiating factors.

A slow progressive death of neurons is the hallmark of neurodegenerative diseases, such as glaucoma. A therapeutic candidate, erythropoietin (EPO), has shown promise in many models of these diseases; however, it also causes polycythemia (an increase in hematocrit or overproduction of red blood cells), a potentially lethal side effect.

To address this deficiency in EPO treatment, the inventors have developed a novel mutant form of EPO that is neuroprotective but no longer erythropoietic. A single amino acid alteration (arginine to glutamate at position 76; R76E) was made which resulted in a mutant EPO that retained the neuroprotective qualities while reducing the erythropoietic activity. As described in the Examples below, a single intramuscular injection of recombinant adeno-associated virus carrying a DNA sequence encoding EPO-R76E (rAAV.CMV.EpoR76E) protects retinal ganglion cells (RGCs) in a mouse model of glaucoma without inducing polycythemia. This systemic treatment not only protects the retinal ganglion cell somata located within the retina, it also preserved axonal projections within the optic nerve, while maintaining the hematocrit within normal limits. The rescued retinal ganglion cells retained their visual function demonstrated by flash visual evoked potentials. Unlike the wild-type EPO, the mutant version disclosed herein does not increase hematocrit levels, and yet is just as effective at protecting the retinal ganglion cell bodies and axons and preserving visual function (based on measurement of visual evoked potentials).

Full length or pro EPO-R76E is processed by the cells and therefore is automatically converted from the pro to the active form during normal production of the protein by the cell. EPO has been reported in many forms, and hence there exists a potential for confusion regarding numbering of the amino acid residues. In certain databases, it is not taken into account that EPO is processed in the cell into an active form by removal of the first 27 amino acids and removal of the last amino acid. Also, the endogenous processing of EPO is not reported in a separate paper. Rather, it is mentioned in some papers in which the authors characterize the 3D structure of EPO (Wen et al.). For purposes of the present invention, the mutation (R103E in the pro form of EPO) is R76E in the active form of EPO, and it is this numbering, for the active form, that is used in all subsequent papers and in patent literature. This is further confirmed because—in the counting for the active form of EPO—there is a serine (S) at position 100 and this mutant is reported in the literature and in patents. With the pro form numbering there is no serine at position 100 (actually position 73 in the active form).

Thus, the present disclosure provides unique compositions and methods for the treatment of neuronal degeneration such as retinal degeneration causing disorders including, but not limited to, glaucoma. More specifically, the present disclosure provides novel compositions and methods that enable the protection of axons, and not simply methods limited to the protection of retinal ganglion cell bodies. The present disclosure further provides for the treatment of disorders associated with retinal degeneration such as glaucoma.

In contrast to other therapies that have been used in the past, the disclosed compositions and methods efficacy is its axonal protection. Other therapeutics are effective for the protection of cell bodies, but protection of cell bodies is not necessarily equivalent to axon protection. The significance of axon protection is that, in order for vision to be restored or maintained, axons must also be protected—simply keeping the cell bodies alive is not adequate for enabling vision.

Further, the protection of cell bodies and protection of axons is not obvious, or necessarily to be expected from the same therapeutic agent. For example, it has been demonstrated that blocking apoptosis (using Bax−/− mice) preserves retinal ganglion cell bodies and proximal axons (the nerve fiber layer), but that the axons past the lamina (posterior to the eye ball) are degenerated/dead (Howell et al. *J Cell Biol,* 2007 Dec. 13: 179(7):1523-37). Howell et al. also demonstrate that the axons degenerate by Wallerian degeneration and that the cell bodies die by apoptosis. Others conducting research in the area of DBA/2J glaucoma neuroprotection show protection of the cell bodies, without protection of the axons/optic nerve. See for example: Ward et al., (*J. Pharm Sci.* 2007 March 96(3):558-68); Zhong et al., (*Invest Ophthalmol V is Sci* 2007 March 48(3):1212-8); Zhou et al., (*Dev Neurobiol.* 2007 April 67(5):603-16); Zhou et al., (*Mol Vis.* 2009; 15:438-50). Again, these and other findings demonstrate that simply because an agent can protect the retinal ganglion cell bodies it does not mean that the agent protects the axons. In fact, quite the opposite is true. Most factors appear to only block apoptosis of the cell bodies without affecting the axons at all. This is why those treatments are not long-lasting and why they do not return useful vision.

One skilled in the art would not expect that neuroprotective molecules that protect RGC bodies necessarily protect or reduce detrimental effect on axons. Accordingly, it is a surprising and unexpected finding that EPO-R76E mitigates the degeneration of axons and prevents apoptosis of cell bodies (i.e. retinal ganglion cell bodies RGC). Memantine, for example, blocks cell death of the RGCs, but no effect on axons is reported (Ju et al., *IOVS,* 2009); Melatonin blocks cell death, but has no reported effect on axons (Siu et al., *Br. J. Ophthal.,* 2004); Copolymer 1 blocks cell death, however no images of axons or functional measurements are reported (Bakalash et al., *IOVS,* 2003; Ben Simon et al., *Am J Ophthalmol.,* 2006); and, BDNF and LINGO-1 block cell death in a laser-induced model of glaucoma, with no positive report on axons.

Yet another surprising finding of the present invention relates to the fact that the observed neuroprotection is independent of the intraocular pressure (protection is obtained despite a continued high IOP). Most therapeutics currently in use rely on decreasing IOP as a key component in alleviating symptoms associated with disorders resulting from retinal degeneration such as glaucoma.

As detailed in the Example section, to provide long-term therapy, a cDNA encoding the mutant EPO was packaged into rAAV. Intramuscular delivery of the rAAV.EpoR76E resulted in very high levels of EPO-R76E in the serum for the entire length of the study, 90 days. And surprisingly, despite the over-expression of EPO-R76E, hematocrit levels were not significantly altered. The photoreceptors were protected by rAAV-mediated systemic delivery of EPO-R76E in the rds/rds mouse.

As further discussed in the Example section, optimal neuroprotection using EPO-R76E was obtained via intramuscular injection of a viral construct containing DNA encoding EPO-R76E. The results demonstrate that intramuscular gene delivery is a safe and effective means of protecting photoreceptors from cell death, long-term, without performing an intraocular injection. In alternative embodiments, EPO-R76E protein may also be delivered via intravenous routes.

B. Mutant Erythropoietin

Disclosed herein are mutants of EPO that are capable of providing neuroprotection without causing an unsafe increase in hematocrit levels. The disclosed EPO mutants include a mutation in at position 76, in which the native arginine residue has been substituted with another amino acid, thus rendering the resulting EPO peptide unable to significantly increase hematocrit levels, while still remaining neuroprotective. In certain examples, a mutant EPO peptide having a mutation at position 76 in the mature EPO polypeptide includes the sequence set forth below as SEQ ID NO: 1, wherein $X_1$ is any amino acid except arginine. APPRLICDSRVLERYLLEAKEAENITTGCAEHC-SLNENITVPDTKVNFYAWK RMEVGQQAVEVWQGLALLSEAVLX$_1$GQALLVNSSQ PWEPLQLHVDKAVSG LRSLTTLLRALGAQKEAISPP-DAASAAPLRTITADTFRKLFRVYSNFLRGKLK LYT-GEACRTGDR (SEQ ID NO: 1). In certain examples, a mutant EPO polypeptide is an active fragment of the peptide set forth as SEQ ID NO: 1 containing residue position number 76, such as a fragment that exhibits neuroprotective activity but does not substantially raise hematocrit levels when administered to a subject. In a specific example, a disclosed mutant EPO protein includes the amino acid sequence set forth as SEQ ID NO: 1, or an active fragment thereof, in which $X_1$ is a glutamic acid and which is set forth below as SEQ ID NO: 2.

(SEQ ID NO: 2)
APPRLICDSRVLERYLLEAKEAENITTGCAEHCSLNENITVPDTKVNFYA

WKRMEVGQQAVEVWQGLALLSEAVLEGQALLVNSSQPWEPLQLHVDKAVS

GLRSLTTLLRALGAQKEAISPPDAASAAPLRTITADTFRKLFRVYSNFLR

GKLKLYTGEACRTGDR.

In some examples, a disclosed mutant EPO polypeptide includes additional mutations at positions 100 and/or 103 of the mature protein. In some examples, a disclosed mutant EPO includes the amino acid sequence set forth as below as SEQ ID NO: 3 (or an active fragment thereof) in which $X_1$ is any amino acid except arginine, $X_2$ is any amino acid except serine and/or $X_3$ is any amino acid except arginine. APPRLICDSRVLERYLLEAKEAENITTGCAEHC-SLNENITVPDTKVNFYAWK RMEVGQQAVEVWQGLALLSEAVLX$_1$GQALLVNSSQ PWEPLQLHVDKAVX$_2$GLX$_3$SLTTLLRALGAQKEAISP PDAASAAPLRTITADTFRKLFRVYSNFLRGK LKLYT-GEACRTGDR (SEQ ID NO: 3). In certain examples, a disclosed mutant EPO includes the amino acid sequence set forth as SEQ ID NO: 3 (or an active fragment thereof) in which $X_1$ is glutamic acid, $X_2$ is any amino acid except serine and/or $X_3$ is any amino acid except arginine. In specific examples, a disclosed mutant EPO includes the amino acid sequence set forth as SEQ ID NO: 3 (or an active fragment thereof) in which $X_1$ is glutamic acid, $X_2$ is a glutamic acid and/or $X_3$ is a glutamic acid.

In some embodiments, a disclosed a mutant EPO peptide further includes the leader sequence set forth as SEQ ID NO: 4 (MGVHECPAWLWLLLSLLSLPLGLPVLG, SEQ ID NO: 4) which can be cleaved during port translational processing to produce the mature EPO peptide from the pro-peptide. In certain examples, a mutant EPO peptide having a mutation at position 76 in the mature EPO polypeptide includes the sequence set forth below as SEQ ID NO: 5, wherein $X_1$ is any amino acid except arginine. MGVHECPAWLWLLLSLLSLPLGLPVLGAPPRLICD-SRVLERYLLEAKEAENITT GCAEHCSLNENITVPDT-KVNFYAWKRMEVGQQAVE VWQGLALLSEAVLX$_1$GQALLVNSSQPWEPLQLHVD KAVSGLRSLTTLLRALGAQKEAISPPDAASA APLRTI-TADTFRKLFRVYSNFLRGKLKLYTGEACRTGDR (SEQ ID NO: 5). In certain examples, a mutant EPO peptide is an active fragment of the peptide set forth as SEQ ID NO: 5 containing residue position number 76, such as a fragment that exhibits neuroprotective activity but does not substantially raise hematocrit levels when administered to a subject. In a specific example, a disclosed mutant EPO protein includes the amino acid sequence set forth as SEQ ID NO: 5, or an active fragment thereof, in which $X_1$ is a glutamic acid and which is set forth below as SEQ ID NO: 6.

(SEQ ID NO: 6)
MGVHECPAWLWLLLSLLSLPLGLPVLGAPPRLICDSRVLERYLLEAKEAE

NITTGCAEHCSLNENITVPDTKVNFYAWKRMEVGQQAVEVWQGLALLSEA

VLEGQALLVNSSQPWEPLQLHVDKAVSGLRSLTTLLRALGAQKEAISPPD

AASAAPLRTITADTFRKLFRVYSNFLRGKLKLYTGEACRTGDR.

In some examples, a disclosed mutant EPO peptide includes additional mutations at positions 100 and/or 103 of the mature protein. In some examples, a disclosed mutant EPO includes the amino acid sequence set forth as below as SEQ ID NO: 7 (or an active fragment thereof) in which $X_1$ is any amino acid except arginine, $X_2$ is any amino acid except serine and/or $X_3$ is any amino acid except arginine.

(SEQ ID NO: 7)
MGVHECPAWLWLLLSLLSLPLGLPVLGAPPRLICDSRVLERYLLEAKEAE

NITTGCAEHCSLNENITVPDTKVNFYAWKRMEVGQQAVEVWQGLALLSEA

VLX$_1$GQALLVNSSQPWEPLQLHVDKAVX$_2$GLX$_3$SLTTLLRALGAQKEAIS

PPDAASAAPLRTITADTFRKLFRVYSNFLRGKLKLYTGEACRTGDR.

In certain examples, a disclosed mutant EPO includes the amino acid sequence set forth as SEQ ID NO: 7 (or an active fragment thereof) in which $X_1$ is glutamic acid, $X_2$ is any amino acid except serine and/or $X_3$ is any amino acid except arginine. In specific examples, a disclosed mutant EPO includes the amino acid sequence set forth as SEQ ID NO: 7 (or an active fragment thereof) in which $X_1$ is glutamic acid, $X_2$ is a glutamic acid and/or $X_3$ is a glutamic acid. In a specific example, a EPO peptide including the leader sequence is set forth below as SEQ ID NO: 8.

(SEQ ID NO: 8)
MGVHECPAWLWLLLSLLSLPLGLPVLGAPPRLICDSRVLERYLLEAKEAE

NITTGCAEHCSLNENITVPDTKVNFYAWKRMEVGQQAVEVWQGLALLSEA

VLEGQALLVNSSQPWEPLQLHVDKAVSGLRSLTTLLRALGAQKEAISPPD

AASAAPLRTITADTFRKLFRVYSNFLRGKLKLYTGEACRTGDR.

It is understood that a disclosed mutant EPO polypeptide can deviate slightly from the sequences shown above, such as by the deletion of one, two, or three amino acids from the N- and/or C-terminus of the polypeptide. It is also contemplated that additional amino acid substitutions can be made in the polypeptide, such as the conservative substitutions described in the preceding Summary of Terms as long as the resulting peptide retains neuroprotective activity and does not substantially raise hematocrit levels when administered to a subject. In certain embodiments, a disclosed EPO mutation that in includes a substitution at position 76 of the mature polypeptide is at least 95% identical to a amino acid sequence set forth as any one of SEQ ID NOs. 1-3 and/or 5-8, such as at least 96% identical, at least 97% identical, at least 98% identical, or at least 99% identical to the amino acid sequence set forth as any one of SEQ ID NOs. 1-3 and/or 5-8. The production of polypeptides, such as the disclosed mutation EPO polypeptides, is routine in the art and exemplary methods and techniques are described in the following sections.

C. Polynucleotides Encoding Mutant Erythropoietin

Polynucleotides encoding the mutant EPO polypeptides disclosed herein are also provided, such as nucleic acids encoding polypeptides at least 95% identical to any one of SEQ ID NOs: 1-3 or 5-8. These polynucleotides include DNA, cDNA, and RNA sequences, which encode the mutant EPO polypeptides. In one embodiment, a polynucleotides encoding the mutant EPO polypeptide having a glutamic acid substitution at position number 76 is set forth as SEQ ID NO: 9, below.

(SEQ ID NO: 9)
ATGGGGGTGCACGAATGTCCTGCCTGGCTGTGGCTTCTCCTGTCTCTGCT

CTCGCTCCCTCTGGGCCTCCCAGTCCCGGGCGCCCCACCACGCCTCATCT

GTGACAGCCGAGTCCTGGAGAGGTACCTCTTGGAGGCCAAGGAGGCCGA

GAATGTCACGATGGGCTGTTCCGAAAGCTGCAGCTTGAATGAGAATATC

ACCGTCCCAGACACCAAAGTTAACTTCTATGCCTGGAAGAGGATGGAGG

TCGGGCAGCAGGCTGTAGAAGTCTGGCAGGGCCTGGCCCTGCTCTCAGA

AGCTGTCCTGGAGGGCCAGGCCGTGTTGGCCAACTCTTCCCAGCCTTTCG

AGCCCCTGCAGCTGCACATGGATAAAGCCATCAGTGGCCTTCGCAGCAT

CACCACTCTGCTTCGGGCGCTGGGAGCCCAGGAAGCCATCTCCCTCCCA

GATGCGGCCTCGGCTGCTCCACTCCGAACCATCACTGCTGACACTTTCTG

CAAACTCTTCCGAGTCTACTCCAATTTCCTCCGGGGAAAGCTGAAGCTGT

ACACGGGGGAGGCCTGCAGGAGAGGGGACAGATGA.

Methods for the manipulation and insertion of the nucleic acids of this disclosure into vectors, such as viral vectors, are well known in the art (see for example, Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994).

A nucleic acid encoding a mutant EPO polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule, for example the DNA sequence set forth as SEQ ID NO: 9. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, N.Y., 1989).

The polynucleotides encoding a disclosed mutant EPO polypeptide include recombinant DNA and or RNA which is incorporated into a vector, into an autonomously replicating plasmid, or virus, or into the genomic DNA of a prokaryote or eukaryote, or which exists as a separate molecule (such as a cDNA) independent of other sequences. The nucleotides of this disclosure can be ribonucleotides, deoxyribonucleotides, or modified forms of either nucleotide. The term includes single and double forms of DNA.

DNA sequences encoding a mutant EPO polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding a mutant EPO polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts can include microbial, yeast, insect and mammalian organisms or cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used.

A number of viral vectors have been constructed, that can be used to express the disclosed mutant EPO polypeptides, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-

256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158: 67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In particular embodiments, the a nucleic expressing a mutant EPO polypeptide is packaged into a recombinant adeno-associated virus (rAAV) for example a rAAV of any serotype or a hybrid of one more than one serotype, for example AVV serotype 1, 2, 3, 4, 5, 6, 7, 8, 9 or hybrids thereof, such as 2/5, 2/8 and 2/1 hybrids. In particular examples, a nucleic expressing a mutant EPO polypeptide is packaged in pAAV2 backbone downstream of a cytomegalovirus promoter (CMV), for example producing pAAV2.CMV.EpoR76E, a pAAV2/5 backbone downstream of a CMV promoter, for example producing pAAV2/5.CMV.EpoR76E, a pAAV2/8 backbone downstream of a CMV promoter, for example producing pAAV2/8.CMV.EpoR76E, a pAAV2/1 backbone downstream of a tet promoter, for example producing pAAV2/1.epoR76E.tet.egfp.

Nucleic acid molecules encoding the disclosed mutant EPO polypeptides can be prepared by chemical peptide synthesis. Nucleic acid molecules encoding the mutant EPO polypeptides proteins of this disclosure can be prepared by cloning techniques. Examples of appropriate cloning and sequencing techniques, and instructions sufficient to direct persons of skill through many cloning exercises are found in Sambrook et al., *Molecular Cloning: A Laboratory Manual* (2nd Ed.), Vols. 1-3, Cold Spring Harbor Laboratory (1989), Berger and Kimmel (eds.), *Guide to Molecular Cloning Techniques*, Academic Press, Inc., San Diego Calif. (1987), or Ausubel et al. (eds.), *Current Protocols in Molecular Biology*, Greene Publishing and Wiley-Interscience, N.Y. (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH® laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), INVITROGEN™ (San Diego, Calif.), and Applied Biosystems (Foster City, Calif.), as well as many other commercial sources known to one of skill.

In some embodiments, the peptides of this disclosure are produced recombinantly, for example from cells transformed or transfected with polynucleotides encoding the peptides or portion thereof. Methods for the manipulation and insertion of the nucleic acids encoding the peptides of this disclosure or portions thereof into vectors for the expression of polypeptides are well known in the art (see for example, Sambrook et al., *Molecular Cloning, a Laboratory Manual,* 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994).

Methods and plasmid vectors for producing proteins and peptides in bacteria are described in Sambrook et al. (Molecular Cloning: A Laboratory Manual, Cold Spring Harbor, N.Y., 1989, Chapter 17). Such proteins and peptides may be made in large amounts, are easy to purify. Proteins and proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (Molecular Cloning: A Laboratory Manual, Cold Spring Harbor, N.Y., 1989) and are well known in the art. Often, proteins expressed at high levels are found in insoluble inclusion bodies. Methods for extracting proteins from these aggregates are described by Sambrook et al. (Molecular Cloning: A Laboratory Manual, Cold Spring Harbor, N.Y., 1989, Chapter 17).

Vector systems suitable for the expression of proteins and peptides include the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). The DNA sequence can also be transferred to other cloning vehicles, such as other plasmids, bacteriophages, cosmids, animal viruses, and yeast artificial chromosomes (YACs) (Burke et al., *Science* 236:806-12, 1987). These vectors may then be introduced into a variety of hosts including somatic cells, and simple or complex organisms, such as bacteria, fungi (Timberlake and Marshall, *Science* 244:1313-7, 1989), invertebrates, plants (Gasser and Fraley, Science 244:1293, 1989), and mammals (Pursel et al., *Science* 244:1281-8, 1989).

Various yeast strains and yeast-derived vectors are commonly used for expressing and purifying proteins, for example, *Pichia pastoris* expression systems are available from INVITROGEN™ (Carlsbad, Calif.). Such systems include suitable *Pichia pastoris* strains, vectors, reagents, transformants, sequencing primers and media.

Non-yeast eukaryotic vectors can also be used for expression of mutant EPO polypeptides. Examples of such systems are the well known Baculovirus system, the Ecdysone-inducible mammalian expression system that uses regulatory elements from *Drosophila melanogaster* to allow control of gene expression, and the Sindbis viral expression system that allows high level expression in a variety of mammalian cell lines. These expression systems are available from INVITROGEN™.

For expression in mammalian cells, the cDNA sequence may be ligated to heterologous promoters, such as the simian virus SV40, promoter in the pSV2 vector (Mulligan and Berg, 1981, *Proc. Natl. Acad. Sci. USA* 78:2072-6), and introduced into cells, such as monkey COS-1 cells (Gluzman, *Cell* 23:175-82, 1981), to achieve transient or long-term expression. The stable integration of the chimeric gene construct may be maintained in mammalian cells by biochemical selection, such as neomycin (Southern and Berg, *J. Mol. Appl. Genet.* 1:327-41, 1982) and mycophoenolic acid (Mulligan and Berg, *Proc. Natl. Acad. Sci. USA* 78:2072-6, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit the transcription of the cDNA eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan and Berg, *Proc. Natl. Acad. Sci. USA* 78:2072-6, 1981; Gorman et al., *Proc. Natl. Acad. Sci. USA* 78:6777-81, 1982). The level of expression of the cDNA can be manipulated with this type of vector, either by using promoters that have different activities (for example, the baculovirus pAC373 can express cDNAs at high levels in *S. frugiperda* cells (Summers and Smith, 1985, Genetically Altered Viruses and the Environment, Fields et al. (Eds.) 22:319-328, Cold Spring Harbor Laboratory Press, Cold Spring Harbor, N.Y.) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-6, 1981) or neo (Southern and Berg, *J. Mol. Appl. Genet.* 1:327-41, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human, or other mammalian cells, is now a conventional technique. The vectors are introduced into the recipient cells as pure DNA (transfection) by, for example, precipitation with calcium phosphate (Graham and vander Eb, 1973, *Virology* 52:466) or strontium phosphate (Brash et al., *Mol. Cell Biol.* 7:2013, 1987), electroporation (Neumann et al., *EMBO J.* 1:841, 1982), lipofection (Felgner et al., *Proc. Natl. Acad. Sci. USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-7, 1980), or pellet guns (Klein et al, *Nature* 327:70, 1987). Alternatively, the cDNA can be introduced by infection with virus vectors. Systems are developed that use, for example, retroviruses (Bernstein et al., *Gen. Engrg.* 7:235, 1985), adenoviruses (Ahmad et al., *J. Virol.* 57:267, 1986), or Herpes virus (Spaete et al., *Cell* 30:295, 1982).

Using the above techniques, the expression vectors containing mutant EPO polypeptides can be introduced into human cells, primate cells, mammalian cells from other species, or non-mammalian cells as desired. The choice of cell is determined by the purpose of the treatment. For example, monkey COS cells (Gluzman, *Cell* 23:175-82, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

Mutant EPO peptides also may be produced, for example by chemical synthesis by any of a number of manual or automated methods of synthesis known in the art. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/ hydroxybenzotriazole or 2-(1H-benzo-triazol-1-yl)-1,1,3,3-tetramethyluronium hexafluorophosphate/ hydroxybenzotriazole (HBTU/HOBT), and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. *Solid Phase Peptide Synthesis, IRL Press: Oxford,* 1989.

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5-3 hours at room temperature.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

C. Therapeutic Methods and Pharmaceutical Compositions

In accordance with the various treatment methods of the disclosure, the disclosed mutant EPO polypeptides and nucleic acids encoding such polypeptides can be delivered to a subject in a manner consistent with conventional methodologies associated with management of the disorder for which treatment or prevention is sought. The disclosed mutant EPO polypeptides, or a nucleic acid molecule encoding the disclosed mutant EPO polypeptides, are administered to a subject in order to treat a neurodegenerative disorder and/or neuronal degeneration, such as glaucoma, Alzheimer's disease, Parkinson's Disease, spinal cord injury, neuropathy associated with exposure to a neurotoxic solvent that form a gamma-diketone compound (such as n-hexane), solvent (1,2-diethylbenzene and/or n-hexane, or gamma-diketone) neuropathy, or neuropathies associated with production of protein adducts molecules (such as gamma-keto-aldehydes, oxidative metabolities of arachidonic acid), ALS (Lou Gehrig's), diabetic neuropathy, uremic neuropathy (kidney failure), dementia, Corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia disease, multiple sclerosis, konzo, tropical ataxic neuropathy, ALS/PDC, Lathyrsism, primary lateral sclerosis, or spinal muscular atrophy. In particular examples, the disclosed mutant EPO polypeptides and nucleic acids encoding such polypeptides are administered to a subject in order to treat glaucoma.

Typical subjects intended for treatment with the compositions and methods of the present disclosure include humans, as well as non-human primates and other animals. To identify subjects for prophylaxis or treatment according to the methods of the disclosure, accepted screening methods are employed to determine risk factors associated with a targeted or suspected disease of condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art. These and other routine methods allow the clinician to select patients in need of therapy using the methods and pharmaceutical compositions of the disclosure. In accordance with these methods and principles, a disclosed composition can be administered according to the teachings herein as an independent prophylaxis or treatment program, or as a follow-up, adjunct or coordinate treatment regimen to other treatments.

In exemplary applications, compositions are administered to a subject suffering from a neurodegenerative disorder and/or neuronal degeneration or at risk of neurodegenerative disorder and/or neuronal degeneration. In other applications, the compositions disclosed herein can be administered prophylactically. Typically, the composition is administered in an amount sufficient to treat the neurodegenerative disorder and/or neuronal degeneration without substantially increasing the hematocrit levels over the subject. In specific examples, an effective amount of a disclosed composition is administered to a subject to treat disorders associated with retinal degeneration such as glaucoma. As disclosed herein, the disclosed compositions and methods enable the protection of axons, and not simply limited to the protection of retinal ganglion cell bodies, and for the treatment of disorders associated with retinal degeneration such as glaucoma.

In some examples, administration of the disclosed compositions inhibits Wallerian degeneration of axons. In some examples, administration of the disclosed compositions inhibits apoptosis of neuronal cell bodies. In some examples, administration of the disclosed compositions preserves visual function as measured by visual evoked potentials (demonstrating that the retinal ganglion cells could still receive a signal initiated by the photoreceptors in the outer retina and send it to the visual cortex in the brain). In some examples, administration of the disclosed compositions is independent of the intraocular pressure.

Administration induces a sufficient response to treat the neurodegenerative disorder, for example, to inhibit and/or reduce the signs and/or symptoms of the neurodegenerative disorder. Amounts effective for this use will depend upon the severity of the disease, the general state of the subject's health, and the robustness of the subject. A therapeutically effective amount is that which provides either subjective relief of a symptom(s) or an objectively identifiable improvement as noted by the clinician or other qualified observer.

A disclosed mutant EPO polypeptide or nucleic acid encoding a disclosed mutant EPO polypeptide can be administered by any means known to one of skill in the art (see e.g. Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, or intravenous injection, but even oral, nasal, or anal administration is contemplated. In one embodiment, administration is by subcutaneous or intramuscular injection. To extend the time during which the disclosed mutant EPO polypeptide or nucleic acid encoding a disclosed mutant EPO polypeptide is available to stimulate a response, the mutant EPO polypeptide or nucleic acid encoding a disclosed mutant EPO polypeptide can be provided as an implant, an oily injection, or as a particulate system. The particulate system can be a microparticle, a microcapsule, a microsphere, a nanocapsule, or similar particle. (see, e.g., Banga, supra).

Oil can be included in the composition to promote the retention of the mutant EPO polypeptide or nucleic acid encoding a disclosed mutant EPO polypeptide in an oil-in-water emulsion, for example, to provide a vehicle for the desired mutant EPO polypeptide disclosed mutant EPO polypeptide or nucleic acid encoding a disclosed mutant EPO polypeptide. Preferably, the oil has a melting temperature of less than 65° C. such that emulsion is formed either at room temperature (about 20° C. to 25° C.) or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse effects, such as granulomas, are evident upon use of the oil.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In another embodiment, a pharmaceutical composition includes a nucleic acid encoding a disclosed mutant EPO polypeptide. A therapeutically effective amount of the nucleic acid can be administered to a subject in order to generate the desired response. In one specific, non-limiting example, a therapeutically effective amount of a nucleic acid encoding a disclosed mutant EPO polypeptide is administered to a subject to treat or prevent or inhibit a neurodegenerative disorder, such as those described above.

One approach to administration of nucleic acids is direct immunization with plasmid DNA, such as with a mammalian expression plasmid. As described above, the nucleotide sequence encoding the disclosed mutant EPO polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin).

In another approach to using nucleic acids for immunization, a disclosed EPO polypeptide can also be expressed by attenuated viral hosts or vectors or bacterial vectors. Recombinant vaccinia virus, adeno-associated virus (AAV), herpes virus, retrovirus, cytogmeglo virus, or other viral vectors can be used to express the peptide or protein. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991). As disclosed herein AAV vectors have been shown to be effective in the delivery of mutant EPO.

In some embodiments, a nucleic acid encoding a disclosed mutant EPO polypeptide is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, e.g., U.S. Pat. No. 5,589,466).

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

The compositions or disclosed herein may be included in pharmaceutical compositions (including therapeutic and prophylactic formulations), typically combined together with one or more pharmaceutically acceptable vehicles and, optionally, other therapeutic ingredients).

To formulate the pharmaceutical compositions, the compositions can be combined with various pharmaceutically acceptable additives, as well as a base or vehicle for dispersion of the compositions. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The composition can be dispersed in a base or vehicle, which can include a hydrophilic compound having a capacity to disperse the composition, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films, for examples for direct application to a mucosal surface.

The composition can be combined with the base or vehicle according to a variety of methods, and release of the vaccine can be by diffusion, disintegration of the vehicle, or associated formation of water channels. In some circumstances, the compositions is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering a disclosed mutant EPO polypeptide or nucleic acid encoding a disclosed mutant EPO polypeptide can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the composition can be brought about by including in the composition an agent which delays absorption, for example, monostearate salts and gelatin.

In certain embodiments, the composition can be administered in a time-release formulation, for example in a composition that includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin.

When controlled release formulations are desired, controlled release binders suitable for use in accordance with the disclosure include any biocompatible controlled release material which is inert to the active agent and which is capable of incorporating the vaccine and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compositions in the required amount in an appropriate solvent with one or a combination of ingredients enumerated herein, as required, followed by filtered sterilization. Generally, dispersions are prepared by incorporating the vaccine and/or other biologically active agent into a sterile vehicle that contains a basic dispersion medium and the required other ingredients from those enumerated herein. In the case of sterile powders, methods of preparation include vacuum drying and freeze-drying which yields a powder of the vaccine plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Determination of effective dosages in this context is typically based on animal model studies followed by human clinical trials, and it is guided by administration protocols that significantly reduce the occurrence or severity of targeted disease symptoms or conditions in the subject. Suitable models in this regard include, for example, murine, rat, porcine, feline, ferret, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of composition.

The actual dosage of the disclosed mutant EPO polypeptide or nucleic acid encoding a disclosed mutant EPO polypeptide will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the vaccine for eliciting the desired activity or biological response in the subject. Dosage regimens can be adjusted to provide an optimum prophylactic or therapeutic response. As described above in the forgoing listing of terms, a effective amount is also one in which any toxic or detrimental side effects of the disclosed mutant EPO polypeptide or nucleic acid encoding a disclosed mutant EPO polypeptide is outweighed in clinical terms by therapeutically beneficial effects. A non-limiting range for a therapeutically effective amount of a disclosed mutant EPO polypeptide or nucleic acid encoding a disclosed mutant EPO polypeptide within the methods and formulations of the disclosure is about 0.01 mg/kg body weight to about 10 mg/kg body weight, such as about 0.01 mg/kg, about 0.02 mg/kg, about 0.03 mg/kg, about 0.04 mg/kg, about 0.05 mg/kg, about 0.07 mg/kg, about 0.09 mg/kg, about 0.1 mg/kg, about 0.2 mg/kg, about 0.3 mg/kg, about 0.4 mg/kg, about 0.5 mg/kg, about 0.7 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight.

An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the disclosed compositions.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

The following examples are provided to illustrate certain particular features and/or embodiments. These examples should not be construed to limit the disclosure to the particular features or embodiments described.

EXAMPLES

Example 1

Materials and Methods

Generation and In Vitro Testing of pAAV2/5.CMV.S71E and pAAV2/5.CMV.R76E: The pAAV-TF.rhEpo2.3w (ARIAD® Pharmaceuticals, Cambridge, Mass.) was digested with EcoRI and Sac1 to release the rhesus EPO sequence that was then ligated into pBluescript11 KS+ (Stratagene, La Jolla, Calif.). The QuickChange™ multi site-directed mutagenesis kit (Stratagene, La Jolla, Calif.) was used according to manufacturer's instruction, using the following primers: CTCAGAAGCTGTCCTGGAGGGC-CAGGCCG (SEQ ID NO: 10) for R76E and GGGCCTG-GCCCTGCTCGAAGAAGCTGTCC (SEQ ID NO: 11) for S71E. The mutated EPO sequences were PCR amplified using F-primer GTCATATGCGGCCGCATGGGGGTG-CACGAATG (SEQ ID NO: 12) and R-primer GATC-CAAGCTTTCATCTGTCCCCTCTCCTGCA (SEQ ID NO: 13) and Extensor hi-fidelity PCR enzyme mix (Thermo Scientific, Waltham, Mass.) and cloned into the pAAV2 backbone downstream of the cytomegalovirus promoter (CMV), producing pAAV2.CMV.EpoR76E and pAAV2.CMV.EpoS71E vectors. The mutations were confirmed by sequencing.

The EPO mutant plasmids (1 mg of each) were transfected to human epithelial kidney (HEK) 293 cells (ATCC, Manassas, Va.) using PrimeFect1 DNA transfection reagent according to the manufacturers protocol (Cambrex, East Rutherford, N.J.). To test the viral vectors, 70% confluent HEK 293 cells were transduced with each vector separately at a multiplicity of infection (MOI) of 10. Media from the respective transfections or transductions were collected 72 hours later and used for Enzyme-linked immunosorbent assay (ELISA) or Western Blot analysis.

Generation of rAAV: The viral vectors were generated by triple transfection into HEK293 cells, purified by cesium chloride gradient, and titered by real-time quantitative PCR. The final titers were: $1.3 \times 10^{14}$ vg/ml for rAAV2/5.CMV.EpoS71E; and $8.0 \times 10^{13}$ vg/ml for rAAV2/5.EpoR76E. The viral vectors were diluted and dialyzed with 7000 MWCO Slide-A-Lyzer mini dialysis units (Pierce, Rockford, Ill.) in lactated Ringers buffer (Baxter Health Care Corp, Deerfield, Ill.) just prior to use.

Intramuscular injections: Retinal degeneration slow (rds/rds) mice were obtained from Jackson Laboratories (Bar Harbor, Me.). A beveled 10 ml Hamilton syringe was used to deliver $1 \times 10^{12}$ vg in 10 ml into the quadriceps of each mouse at postnatal day (PD) 5.

EPO ELISA: The Quantikine® IVD® Epo ELISA Kit was used according to manufacturer's protocol to detect EPO and EPO-R76E (R&D Systems®, Minneapolis, Minn.). The absorbance at 450 nm with 600 nm reference was detected on a BioTek-µQuant® plate reader (Winooski, Vt.). In some mice, the serum samples were pooled to obtain sufficient material for the ELISA.

Optical coherence tomography: Mice were anesthetized with ketamine/xylazine/urethane (25/10/1000 mg/g body weight). Eyes were dilated with 1% tropicamide. Imaging was performed using the Bioptigen ultra-high resolution imaging system (Bioptigen, Research Triangle Park, N.C.).

Histology: Eyes were preserved overnight in 4% paraformaldehyde in 0.1 M sodium phosphate buffer, pH 7.4, cryopreserved in 30% sucrose in phosphate buffered saline (PBS) overnight at 4° C., and embedded in Tissue Freezing Medium (Triangle Biomedical Sciences, Durham, N.C.). Eyes were serially sectioned on a LEICA CM1800 cryostat (Germany). Ten micron-thick sections were collected such that each slide contained approximately 20 sections representative of the entire eye. The sections were stained with hematoxylin and eosin and imaged on a Nikon Eclipse 80i microscope using a DXM1200C camera (Nikon, Japan). Outer nuclear layer (ONL) thickness was measured every 0.5 mm from the optic nerve head using NIS-Elements AR 3.0 Nikon software and measurements were analyzed using Prism 4.0 software (GraphPad, San Diego, Calif.). Two-way ANOVA was performed to determine the effects of treatment on ONL thickness, p value of 0.05 was considered significant.

Results

Generation of the EPO mutants: An amino acid sequence alignment of human, rhesus, and mouse EPO on two separate databases—ENSMBL and genbank—was performed. Previous publications reported an arginine at position 103 and a serine at position 100; however, an arginine at position 103 and an alanine at position 100 was identified in all species. To further confirm this result, mouse and rhesus cDNA clones were sequenced. In both cases there was an alanine at position 100, confirming the results of the database searches. The discrepancy in reports was due to the pro-form being reported in the databases and the active form being used in the publications, position 103 in the active form would be 130 in the pro form. Thus, R103 was actually R76 in the active form.

Production and detection of EPO mutants: The plasmids were transfected in vitro to demonstrate production and detection of the EPO mutants from the disclosed constructs. High levels of EPO-R76E were detected in the media (631 mU/ml; Table 1). Controls included untransfected cells (0 mU/ml) and pAAV/5.CMV.Epo transfected cells (651 mU/ml).

TABLE 1

In vitro detection of EPO, and EPO-R76E in cell culture media after transfection into ARPE-19 cells.

| Transfection | EPO (mU/ml) |
| --- | --- |
| pAAV.CMV.Epo | 651 |
| pAAV.CMV.EpoR76E | 631 |
| untransduced | 0 |

Intramuscular gene delivery results in high expression of EPO in the serum at postnatal day 90: Eight (±10) mU/ml of EPO in rds/rds was detected in mice injected intramuscularly with rAAV2/5.CMV.eGFP. In contrast, 117 (±77) mU/ml and 332 (±192) mU/ml were detected in the serum of rds/rds mice injected with either rAAV2/5.CMV.Epo or rAAV2/5.CMV.EpoR76E, respectively (Table 2).

TABLE 2

Serum levels of EPO and EPO-R76E in transduced rds/rds mice.

| Treatment | N | EPO (mU/ml) |
| --- | --- | --- |
| rAAV.2/5.CMV.eGFP | 6 | 8 ± 10 |
| rAAV2/5.CMV.Epo | 4 | 117 ± 77 |
| rAAV2/5.CMV.EpoR76E | 4 | 332 ± 192 |

N = number of mice; plus or minus the standard deviation

Systemic delivery of rAAV2/5.CMV.R76E does not result in high hematocrit levels: To assess the ability of the EPO mutants to induce erythropoiesis, the hematocrit was measured at postnatal day 90 (Table 3). The hematocrit in the rAAV2/5.CMV.eGFP treated mice was in the normal range at 46%. In contrast, the hematocrit in the rAAV2/5.CMV.Epo treated mice was increased to 63%. The rAAV2/5.CMV.EpoR76E treated mice had hematocrit levels in the normal range, 52%. To confirm that over-expression of a non-erythropoietic form of EPO does not suppress production of endogenous EPO, the inventors performed real-time quantitative PCR of endogenous mouse EPO in the kidney. There was no difference in mouse EPO message levels in rAAV2/5.CMV.eGFP treated mice and rAAV2/5.CMV.EpoR76E treated mice.

TABLE 3

Hematocrit levels in transduced rds/rds mice.

| Treatment | N | hematocrit |
| --- | --- | --- |
| rAAV.2/5.CMV.eGFP | 22 | 46% |
| rAAV2/5.CMV.Epo | 29 | 63% |
| rAAV2/5.CMV.EpoR76E | 10 | 52% |

N = number of mice

All forms of EPO tested protect the photoreceptors in the rds/rds mouse: Optical coherence tomography was performed in treated and control mice at postnatal day 90 (FIG. 1). In wild-type mice, the ONL is approximately 52 microns thick (FIG. 1A). In contrast the retinas of age-matched rAAV2/5.CMV.eGFP treated rds/rds mice were 29 microns thick (FIG. 1B). Both rAAV2/5.CMV.Epo and rAAV.CMV.EpoR76E treated mice had a thicker ONL, 42 and 38 microns (FIGS. 1C and 1D).

Figure 2:
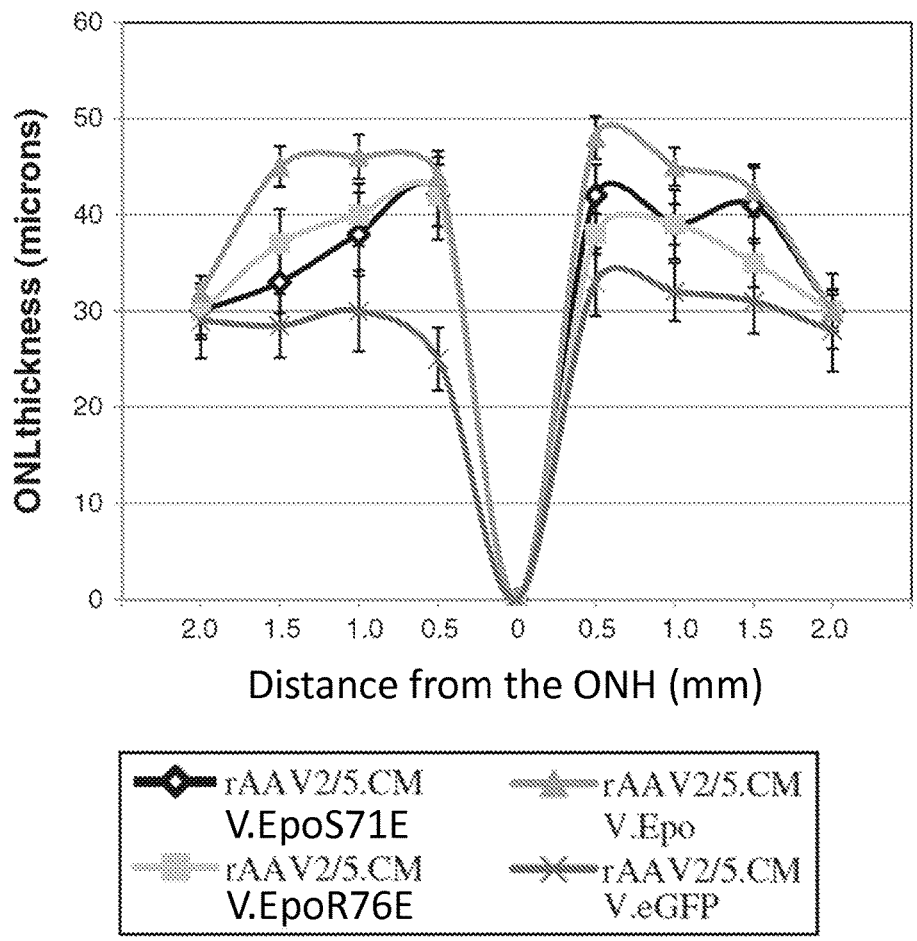
FIG. 2 is a graph showing that treatment with either rAAV2/5.CMV.Epo or rAAV2/5.CMV.EpoR76E in rds/rds mice preserves ONL thickness at postnatal day 90. Measurements of the ONL from histological sections from each treatment group were recorded at 0.5, 1.0, 1.5, and 2 mm from the optic nerve head. The error bars represent the standard error of the mean (S.E.M.).

Histological analysis confirmed the optical coherence tomography results, showing a thicker ONL in the retinas of rAAV2/5.CMV.Epo and rAAV2/5.CMV.EpoR76E treated mice when compared to rAAV2/5.CMV.eGFP treated rds/rds mice (FIGS. 1E-2H). The outer segment defect of the rds/rds mouse was uncorrected by treatment with any vector (FIGS. 1F-2H). ONL thickness was measured at 0.5 mm intervals on either side of the optic nerve head (FIG. 2). A significant difference in ONL thickness was observed in the central portion of the retina. At 0.5 mm and 1.0 mm from the optic nerve head all treatment groups showed a minimum of 21% and 24% increase in ONL thickness ($p<0.01$ and $p<0.001$ respectively) when compared to the control group. At 1.5 mm rAAV2/5.CMV.Epo treatment resulted in a 23% increase in ONL thickness ($p<0.01$). No significant difference was observed at the peripheral sections of the retina (2.0 mm) in any of the treatment groups.

Discussion

Two single amino acid EPO mutants have been reported to be neuroprotective without inducing erythropoiesis, a serine replacement at position 100, and an arginine at position 103. However, is disclosed herein the inventors were unable to identify this amino acid combination despite searching two databases for the EPO sequence in three species, mouse, rhesus, and human, and sequencing EPO cDNA from mouse and rhesus. It was later realized that the databases reported a pro-form of EPO that contained 27 amino acids at the amino terminus. Therefore, rather than making and testing the previously reported mutation at position 103, they fortuitously made a arginine to serine mutation at position 76 (rather than 103).

To provide long-term therapy, the inventors packaged a cDNA encoding the mutant EPO into rAAV. Intramuscular delivery of the rAAV.EpoR76E resulted in very high levels of EPO-R76E in the serum for the entire length of the study, 90 days. Despite the over-expression of EPO-R76E, hematocrit levels were not significantly altered. The photoreceptors were protected by rAAV-mediated systemic delivery of EPO-R76E in the rds/rds mouse.

The results disclosed herein demonstrate that intramuscular gene delivery of EPO-R76E is a safe and effective means of protecting photoreceptors from cell death, long-term, without performing an intraocular injection.

The maximal protection achieved by intramuscular injection of rAAV2/5.CMV.Epo or rAAV.CMV.EpoR76E was preservation of 7 rows of photoreceptors (as compared to 13 rows in wild-type retina) regardless of serotype tested (rAAV2/2) or rAAV2/5 (this study). Both of these serotypes take approximately two weeks to reach high levels of transgene expression. Since gene delivery was performed at PD 7, this means that peak transgene expression was reached at about the same time as peak cell death (PD 20).

Example 2

Materials and Methods

Injections: DBA/2J mice were obtained from Jackson Laboratory (Bar Harbor, Me.). Vectors were produced by the University of Iowa Vector Core (Iowa City, Iowa). A Hamilton syringe was used to deliver 10 µL containing $1 \times 10^{11}$ genome copies of rAAV2/5.CMV.eGFP, rAAV2/5.CMV.Epo, or rAAV2/5.CMV.EpoR76E into the quadriceps of 1-month-old mice. The EPO transgene was derived from rhesus; this was used in previous studies and therefore, for consistency, was used in this study as well (see Example 1 and Sullivan et al., *Neurochem. Res.* 36, 613-618. 2011)

Intraocular pressure: Mice were anesthetized with ketamine/xylazine/urethane (25/10/800 lg/g body weight). Intraocular pressure (IOP) was measured monthly from 5 to 8 months of age, using a TonoLab tonometer (Colonial Medical Supply, Franconia, N.H.). The TonoLab rebound tonometer was used because it is noninvasive, accurate, and reproducible in DBA/2J mice as well as other mouse strains. Mice that developed an IOP of 13 mmHg or greater were used in the analysis.

Immunohistochemistry: At 10 months of age mice were euthanized and eyes were enucleated and stored in 4% paraformaldehyde in 0.1 M phosphate buffer, pH 7.4, at 4° C. Retinas were isolated and incubated in phosphate-buffered saline (PBS) and blocked in 20% normal donkey serum in PBS containing 0.1% Triton™ X-100 and 0.5% bovine serum albumin (BSA) for a minimum of 2 hours at 4° C. The primary antibody, anti-neuronal nuclei (NeuN monoclonal antibody; Chemicon, Temecula, Calif.), was used at a 1:500 dilution and the secondary antibody (Alexa 488; Invitrogen, Carlsbad, Calif.) was used at a 1:200 dilution. Retinas were placed RGC side up, mounted with VECTASHIELD® containing 4,6-diamidino-2-phenylindole (DAPI) (Vector Laboratories, Burlingame, Calif.), and viewed with a Nikon Eclipse TE2000 confocal microscope.

RGC imaging and counts: Retinas were first imaged at 4× magnification and a grid was placed over each retina to randomly select eight locations to be imaged at 40× magnification. The number of NeuN-positive cells in each region was counted manually with ImageJ software (available on the world wide web at rsbweb.nih.gov/ij/, National Institutes of Health, Bethesda, Md.) and MetaMorph® (Universal Imaging/Molecular Devices, Sunnyvale, Calif.).

EPO enzyme-linked immunosorbent analysis and hematocrit: Serum from blood samples was probed for EPO and EPOR76E, using the human EPO Quantikine® IVD®ELISA kit according to the protocol of the manufacturer. It should be noted that the ELISA kit is calibrated against human EPO and has been shown to be 4-fold less sensitive for rhesus versus human EPO, and this was taken into account for calculations presented herein. The absorbance at 450 nm with 600 nm reference was detected with a BioTek-µQuant® plate reader. In some mice the serum samples were pooled in order to obtain sufficient material for the ELISA. Hematocrit was measured by capillary centrifugation.

Optic nerve damage: Optic nerves were isolated and placed in 4% paraformaldehyde in 0.1 M phosphate buffer, pH 7.4, for 1 week at 4° C. Next, samples were postfixed in 1% osmium tetroxide in 0.1 M cacodylate buffer, dehydrated in a graded ethanol series, further dehydrated in propylene oxide, and embedded in EMbed 812 resin (Electron Microscopy Sciences, Hatfield Pa.), cut into 1-lm sections and stained with 1% phenylenediamine in 50% methanol (Sigma-Aldrich, St. Louis, Mo.). Sections were viewed by light microscopy, using an Olympus BX51 microscope (Olympus America, Center Valley, Pa.). Before beginning axon counts, the optic nerve was traced at 10× magnification and the cross-sectional area was automatically calculated with ImageJ software. The entire length from top to bottom of the same cross-section was then imaged, using a 60× oil immersion lens. Approximately the same region of 0.010 mm² was selected from each X 60 image; both live and dead axons were manually counted with ImageJ software. Measurements of the cross-sectional area of the optic nerve were used with axon density to estimate the total number of axons.

F-VEP: After overnight dark adaptation, mice were anesthetized with an intraperitoneal injection of ketamine/xylazine/rethane (25/10/800 lg/g body weight). Although urethane potentiates some ion channels, it was used consistently in all the mice in this study, and therefore it did not affect the relative F-VEP results between groups. Body temperature was maintained at 37° C. with a heading pad. Pupils were dilated with 1% atropine. Platinum needle electrodes (Grass Technologies, West Warwick, R.I.) were placed approximately 3 mm lateral to lambda over the left and right cortex. Flashes of white light at an intensity of 1.0 cd*sec/m² were presented in a Ganzfeld dome (Diagnosys, Lowell, Mass.). The flash frequency was 1 Hz with an inner sweep delay of 500 msec. Each result was an average of 200 sweeps.

Phlebotomy: Mice treated with rAAV2/5.CMV.Epo developed a hematocrit above 90% and therefore had to be phlebotomized weekly. Mice treated with rAAV2/5.CMV.eGFP or rAAV2/5.CMV.EpoR76E were not phlebotomized. Phlebotomy was performed by tail vein clipping or facial vein puncture according to a slightly modified published protocol (see Golde et al., *Lab. Anim.* 34, 39-43, 2005). Briefly, approximately 0.2 ml of blood was collected weekly from the mice. The collection site was alternated between the tail vein and the facial vein. A 20-gauge needle (Becton Dickinson, Franklin Lakes, N.J.) instead of a lancet was used to penetrate the facial vein.

Statistical analysis: One-way analysis of variance (ANOVA) followed by a pair-wise Bonferroni post hoc comparison test, with a p value ≤0.01 considered statistically significant, was used to compare RGC counts, axon counts, N1 amplitude, and P1 amplitude. Statistical analysis was performed with Prism 4.0 software (GraphPad, San Diego, Calif.).

Results

Figure 3:
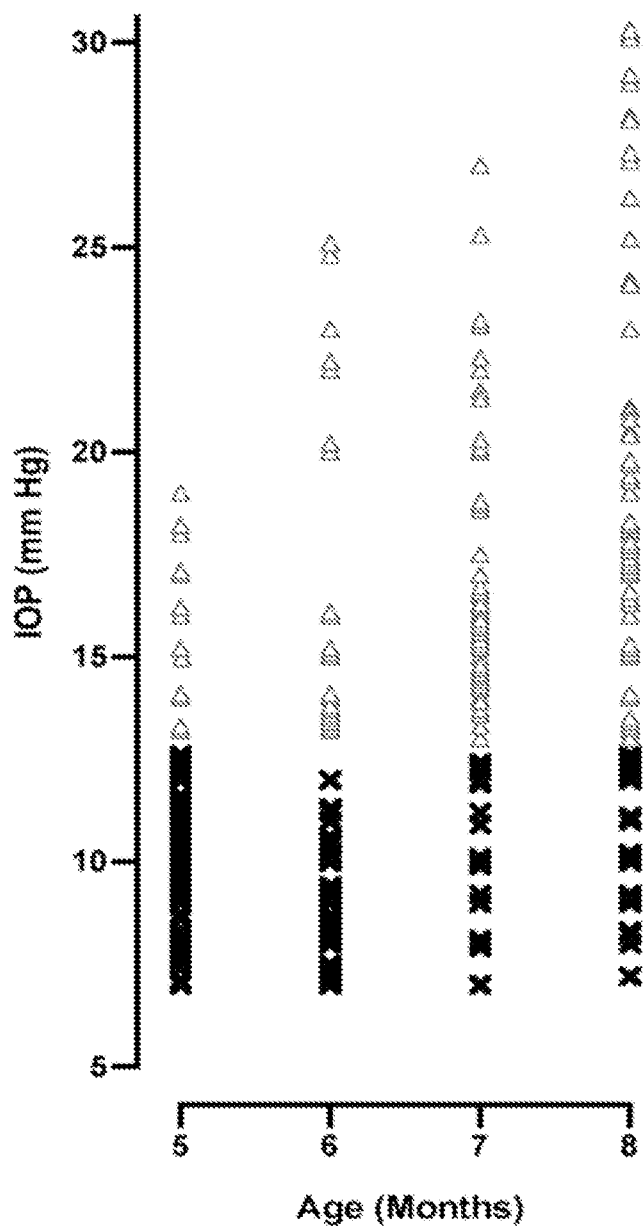
FIG. 3 is a scatter plot showing that intraocular pressure (IOP) was increased in 73/94 DBA/2J mouse eyes by 8 months of age. The scatter plot shows IOP measured monthly by rebound tonometry from DBA/2J mice. Only mice that exhibited an increased IOP above 13 mm Hg ($\Delta$) were considered glaucomatous and entered into the study for further analysis. Mice that exhibited an IOP below 13 mm Hg (X) were not likely to have appreciable retinal ganglion cell (RGC) loss and were not included within the study.

The DBA/2J mouse strain has a variable response in the elevation of IOP; however, when IOP is high neuronal loss occurs. To identify animals with elevated IOP and, therefore, the potential for developing glaucoma, IOP was measured between the ages of 5 and 8 months (FIG. 3). The baseline IOP observed at 3 months of age (12.5 mmHg) was in agreement with previous reports. Once the baseline data were collected a cohort of 47 mice was aged for further study. At 8 months of age, 73 of the 94 eyes had an IOP that exceeded the baseline. All of the eyes with an elevated IOP of ≥13 mmHg were included in the study described this Example to test the effects of EPO and EPO-R76E.

Figure 4A:
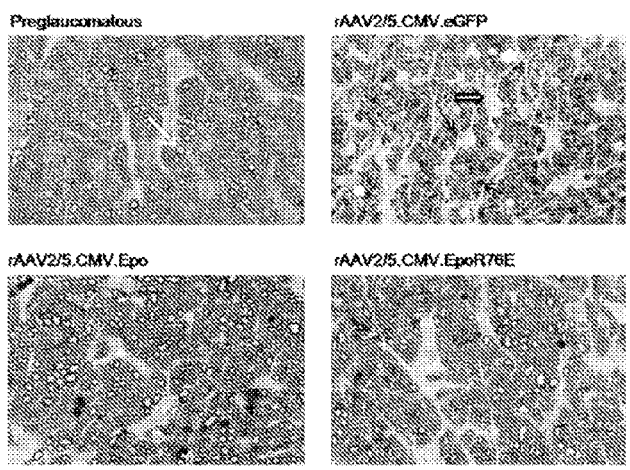
FIGS. 4A and 4B are digital images of micrographs and bar graphs showing that treatment with rAAV2/5.CMV.Epo or rAAV2/5.CMV.EpoR76E protects the optic nerve of DBA/2J mice with exceedingly high IOP ($\geq$25 mmHg) from glaucomatous axonal degeneration.
Figure 4B:
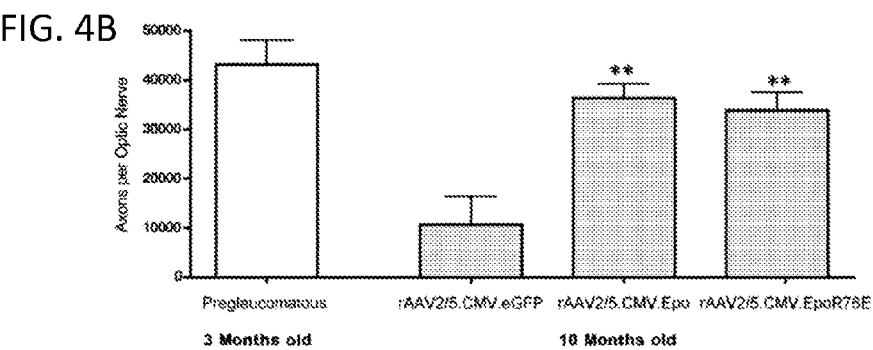

To assess the neuroprotective effects of EPO, the optic nerves were examined for four groups of mice: 3-month-old mice (before the onset of glaucoma) and 10-month-old mice receiving either rAAV2/5.CMV.eGFP (control vector), rAAV2/5.CMV.Epo (Epo vector), or rAAV2/5.CMV.EpoR76E (mutant Epo vector). An obvious difference was observed when examining the cross-sections of the optic nerves (FIG. 4A). There was little degeneration in the optic nerves from young mice and a significant amount of degeneration in the nerves from the older control mice. The effects of both normal EPO and mutant EPO were apparent even at low magnification. Mice treated with either EPO vector had optic nerves that resembled those in young mice without the degeneration observed in aged-matched control mice. To confirm these observations, axons in the optic nerve were counted (FIG. 4B). This quantification confirmed the initial observation, with 70% more surviving axons (p≤0.001) in mice treated with the EPO vector (36,366 axons per nerve) and with the mutant EPO vector (33,841 axons per nerve), than in age-matched control mice (10,648 axons per nerve). There was no significant difference in the number of surviving axons between the EPO-treated optic nerves and nerves from young untreated controls.

Figure 5A:
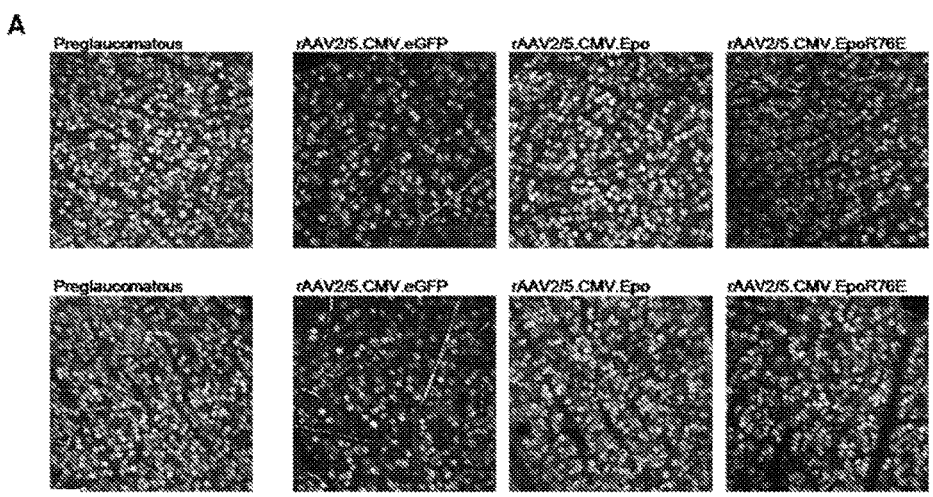
FIGS. 5A and 5B are digital images of micrographs and bar graphs showing that treatment with rAAV2/5.CMV.Epo or rAAV2/5.CMV.EpoR76E protects NeuN-positive cells from glaucomatous cell death.
Figure 5B:
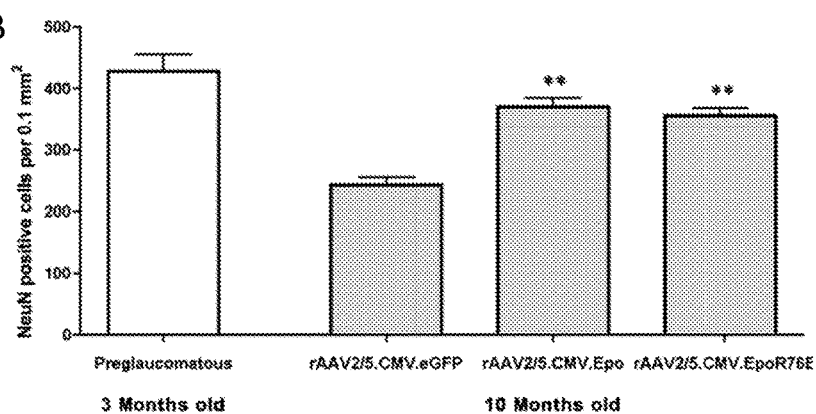

The preservation of the optic nerve mimics the protective effect of both EPO vectors on RGC somata. Retinal flat mounts from all four groups were probed with anti-NeuN (FIG. 5A), a marker for RGCs and some displaced amacrine cells. Young mice had a high NeuN-positive cell density throughout the entire retina whereas older control mice had some areas that were completely devoid of cells. The ganglion cell layer (GCL) of mice treated with either EPO vector closely resembled that of younger mice having a dense population of cells throughout. To directly assess the effects of the treatment, NeuN-positive cells in the GCL were counted (FIG. 5B). The average cell density in young mice (406 cells per 0.1 mm$^2$) was almost 2-fold greater than the density in older control (eGFP-treated) mice (243 NeuN-positive cells per 0.1 mm$^2$). Treatment with the EPO vector (384 cells per 0.1 mm2) or the mutant EPO vector (344 cells per 0.1 mm$^2$) provided a significant level of protection to RGC somata (p≤0.001).

Figure 6:
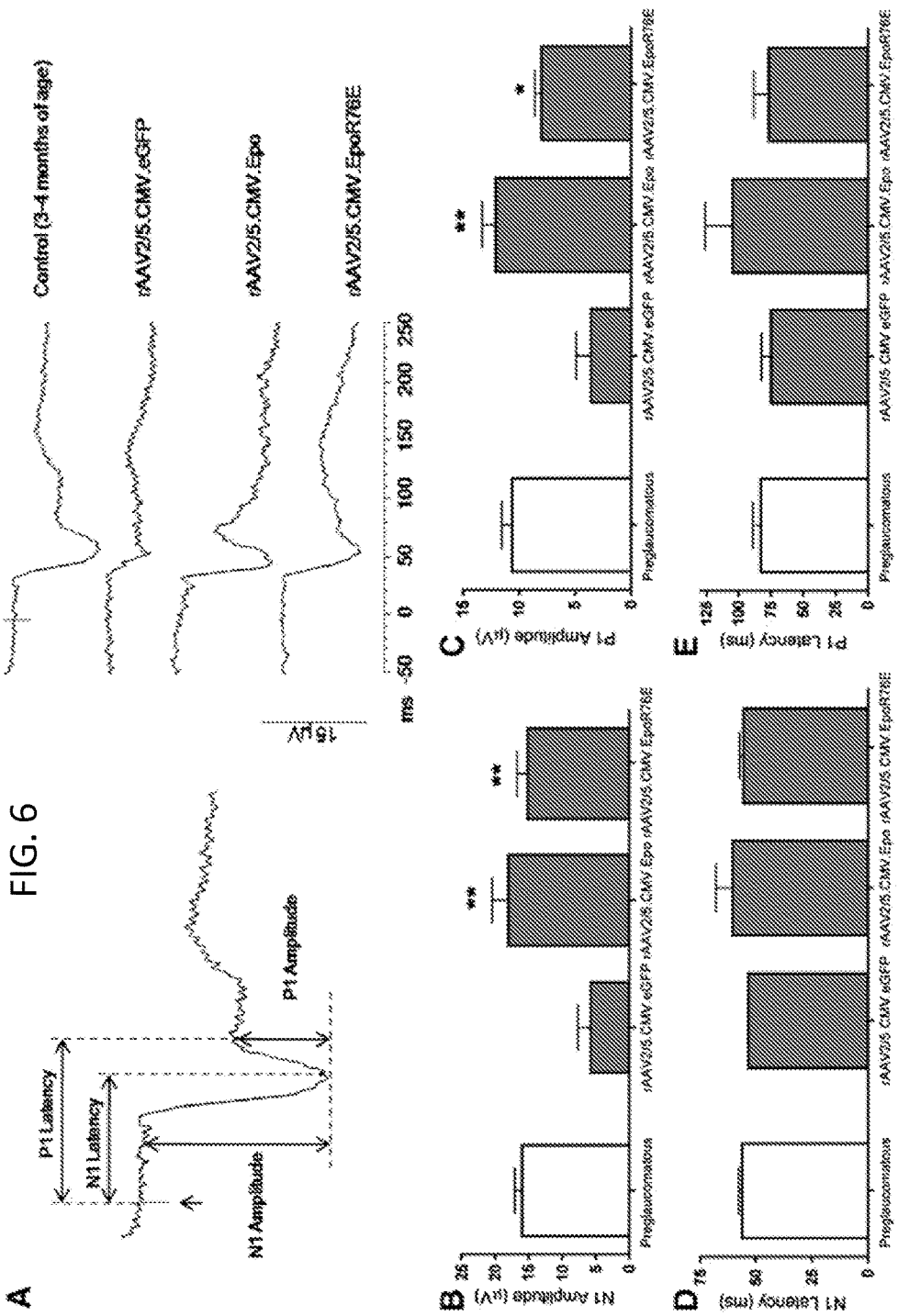
FIGS. 6A-6E are graphs showing that visual function is preserved in 10-month-old DBA/2J mice treated with rAAV2/S.CMV.Epo or rAAV2/5.CMV.EpoR76E.
Figure 7:
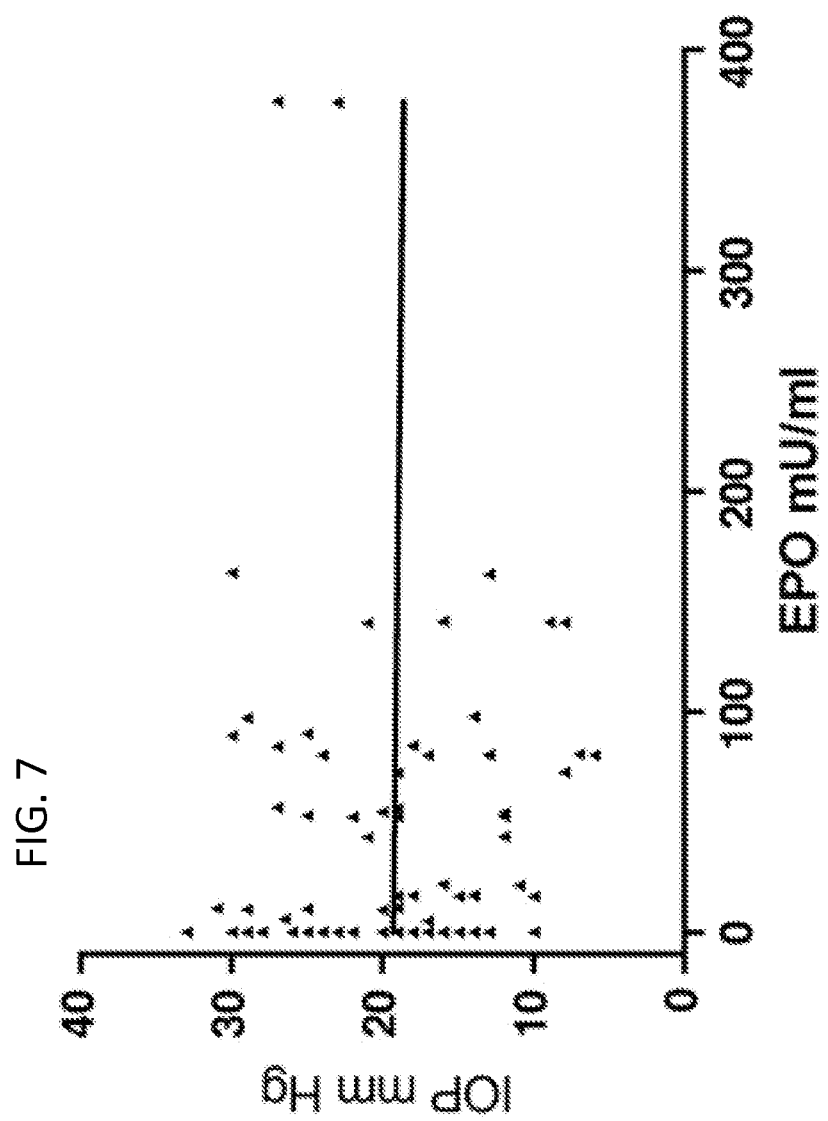
FIG. 7 is a scatter plot showing that erythropoietin (EPO) does not affect the IOP level. The scatter plot shows the IOP levels and serum EPO concentrations from the same 8-month-old DBA/2J mice. As demonstrated by linear regression analysis, there is no correlation between the concentration of EPO and the IOP ($R^2=0.0006674$). The slope of the line=−0.0097.

In addition, there was no significant difference in the number of NeuN-positive cells in the EPO-treated groups as compared with the young controls. In addition to anatomical preservation of both axons and somata, it was found that gene therapy using either EPO vector also preserved visual function in DBA/2J mice. F-VEPs were measured in the visual cortex of DBA/2J mice from all four groups. For a signal to reach the visual cortex both the RGC soma and axon must be intact. The classical N1 and P1 peaks in the F-VEP averaged waveforms were assessed in each treatment group (FIG. 6A). Young DBA/2J mice produced a robust and reproducible signal. By 10 months of age the signal had severely diminished in untreated animals. The decline was particularly notable in the N1 peak; a number of these mice had no detectable signal at all. Ten-month-old mice that received treatment with either the EPO or the mutant EPO vector had visually evoked responses that resembled those of their younger counterparts. The average amplitude and the latency of the N1 and P1 peaks were quantified (FIG. 6B-6E). Young mice had normal N1 (15.7 μV) and P1 (11.3 μV) peak amplitudes (FIGS. 6B and 6C). There was considerable attenuation of the peaks in older control (eGFP-treated) mice (N1, 7.3 μV; P1, 4.2 μV). When animals received either EPO vector there was preservation of the evoked potential amplitude. Ten-month-old mice that received the EPO vector had an N1 peak of 16 μV and a P1 peak of 14 μV. These evoked potentials were significantly higher than those observed in age-matched controls (p≤0.001). Similarly, treatment with the mutant EPO vector also rescued both peaks (N1, 14 μV; P1, 8 μV; p≤0.001 and p≤0.05, respectively). Compared with preglaucomatous controls, the latency of both the N1 and P1 peaks was unchanged in 10-month-old rAAV2/5.CMV.eGFP-treated mice with high IOP (FIGS. 4D and 4E). Treatment with either EPO vector did not statistically significantly alter the latency of either peak, even with the inclusion of one rAAV2/5.CMV.Epo vector treated mouse that had a large increase in the latency time of both peaks (p>0.05; FIGS. 4D and 4E).

rAAV-mediated gene therapy using either the wild-type EPO vector or the EPOR76E mutant vector produced similar amounts of circulating EPO (Table 4). However, long-term treatment with the mutant vector caused little change in hematocrit whereas similar treatment with the wild-type vector caused dangerously high hematocrit levels (Table 4). Treatment with either rAAV2/5.CMV.Epo or rAAV2/5.CMV.-EpoR76E had no statistically significant effect on the IOP (FIG. 7).

Discussion

Glaucoma is the second leading cause of blindness worldwide, affecting nearly 70 million people (Quigley and Broman, 2006). At present, there are no neuroprotective agents clinically available for preventing RGC death or reducing visual field loss in patients with primary open angle glaucoma (Sena et al., 2010). It is disclosed herein, for the first time, that systemic gene delivery of EPO or EPOR76E is capable of protecting both the axons and the RGC somata from glaucomatous damage in DBA/2J mice, and that this morphological protection translates into functional rescue of the visual pathway against glaucomatous damage. In addition, the expression of mutant EPO-R76E provided this protection while maintaining the hematocrit within healthy limits.

The F-VEP is an appropriate electrophysiological test for the study of functional loss due to optic nerve diseases. If either the RGC soma or axon is compromised the signal cannot reach the visual cortex and therefore is not detected by F-VEP. At 2 years of age nearly all untreated DBA/2J mice have advanced glaucoma resulting in few remaining RGCs and almost no detectable cortical activity as measured by F-VEP (see for example Heiduschka et al., Exp. Eye Res. 91, 779-783, 2010). As disclosed herein, it was found that as early as 10 months of age the majority of control mice also had minimal cortical response because of glaucomatous damage. Untreated glaucomatous mice had low but detectable N1 and P1 amplitudes and normal latencies, indicating extensive cell death, but normal synaptic connectivity in the remaining cells. Treatment with either rAAV2/5.CMV.Epo or rAAV2/5.CMV.EpoR76E preserved the F-VEP, which was similar to that observed in young mice. On average, mice receiving these vectors showed complete rescue of the N1 and P1 amplitudes, demonstrating functional protection of the RGC soma and axon.

The results of this study show that systemic delivery of EPO and in particular the R76E EPO mutant, is therapeutic for a broad range of neurodegenerative diseases both in the peripheral and central nervous systems. In many neurodegenerative diseases axonal degeneration precedes death of the neuronal cell body and is often causal of disease symptoms (see for example Coleman and Perry, *Trends Neurosci.* 25, 532-537, 2002 and Raff et al., *Science* 296, 868-871, 2002). This is true of glaucoma, in which progressive axon degeneration is the key pathogenic event causing vision loss and eventual death of the RGC soma. Therefore, demonstration of protection in glaucoma indicates that the disclosed mutant EPO will also protect against many other CNS degenerative diseases. One likely example is Alzheimer's disease, in which there appears to be a genetic link with glaucoma because the rate of glaucoma in Alzheimer's patients is five times higher than that observed in a control population (see for example Bayer et al., *Eur. Neurol.* 47, 165-168, 2002 and McKinnon et al., *Front. Biosci.* 8, 1140-1156, 2003). Also, systemic protein therapy with EPO or nonerythropoietic EPO has been shown to rescue axons in other neurodegenerative models including optic nerve crush (Wang et al., *Chin. Med. J.* (Engl) 122, 2008-2012, 2009), acrylamide-induced neuropathy (Keswani et al., *Ann. Neurol.* 56, 815-826, 2004), chronic constriction injury model (Campana et al., *Eur. J. Neurosci.* 23, 617-626, 2006), sciatic nerve transection (Yin et al., *Am. J. Neuroradiol.* 31, 509-515, 2010), and ALS (Mennini et al., *Mol. Med.* 12, 153-160, s2006).

In the DBA/2J model the primary insult to the optic nerve occurs in the glial lamina as a result of increased IOP. Although the mechanism of the pathogenesis is unknown, several possibilities exist, including mechanical stress, glutamate excitotoxicity, neurotrophin deprivation, oxidative stress, glial cell modulation, and inflammation. As disclosed herein, the protection afforded by EPO is independent of IOP levels. This is of key importance because all currently available therapies are targeted at lowering the IOP, and these therapies have had only mixed success due to poor patient compliance and a subpopulation of patients with normal-tensive glaucoma. In contrast, systemic treatment with EPO-R76E surprisingly blocks progression of the disease at time of treatment regardless of the IOP.

In summary, the results disclosed herein and by others demonstrate that systemic therapy with EPO provides protection in various neurodegenerative models including photoreceptor degeneration, optic nerve crush, acrylamide-induced neuropathy, the chronic constriction injury model, and sciatic nerve transection. Results of the current study have expanded these findings by establishing intramuscular delivery of rAAV2/5.CMV.EpoR76E as an improved therapy without hematopoietic side effects and with the potential to treat glaucoma as well as a broad range of neurodegenerative diseases both in the peripheral nervous system and central nervous system.

Example 3

Materials and Methods

Injections: BALB/cByJ mice were obtained from Jackson Laboratories (Bar Harbor, Me.). Due to its genetic background, the BALB/cByJ mouse is the strain most susceptible to optic nerve crush (see Brines and Cerami, 2008) and therefore serves as an ideal model to study the neuroprotective effects of EPO-R76E. The viral vectors were produced and purified by the University of Iowa or the University of Pennsylvania Vector Cores. A Hamilton syringe was used to deliver 10 µl of: $1\times10^{10}$ genome copies (gc) of rAAV2/5.CMV.eGFP; $1\times10^{10}$ gc rAAV2/5.CMV.Epo; $3\times10^{10}$ gc (dose 1) or $1\times10^{11}$ gc (dose 2) of rAAV2/5.EpoR76E; or $5\times10^{9}$ gc (dose 3) or $1\times10^{12}$ gc (dose 4) of rAAV2/8.EpoR76E into the quadriceps of two month old mice. The Epo transgene was derived from rhesus macaque.

Optic nerve crush: Thirty days after intramuscular vector delivery, mice were anesthetized with ketamine/xylazine/urethane (25/10/1000 µg/g body weight) and a small incision was made in the lateral aspect of the conjunctiva. With a pair of small forceps the edge of the conjunctiva next to the globe was refracted slightly and rotated laterally, allowing visualization of the posterior aspect of the globe and the optic nerve. Viewed under a binocular operating microscope, the surrounding connective tissue and muscle was gently separated from the nerve. The exposed optic nerve was crushed for 10 sec with a pair of Dumont cross-clamp #7 forceps (Roboz, cat. #RS=5027, Gaithersburg, Md.). This instrument was chosen because its spring action applied a moderate yet constant and consistent force to the optic nerve. The forceps were then removed and the eye was allowed to rotate back into place.

Immunohistochemistry: Thirty days post-crush, mice were euthanized and eyes were enucleated and stored in 4% paraformaldehyde in 0.1 M phosphate buffer, pH 7.4 at 4° C. Retinas were isolated and incubated in phosphate buffered saline (PBS) and blocked in 20% normal donkey serum in PBS containing 0.1% Triton-X-100 and 0.5% BSA for a minimum of 2 h at 4° C. The primary antibody, anti-NeuN, a marker for RGCs and some displaced amacrine cells, (Chemicon, Temecula, Calif.) was used at 1:500 and secondary antibody was used at 1:200 (Alexa 488, Invitrogen, Carlsbad, Calif.). Retinas were placed RGC side up, mounted with Vectashield containing DAPI (Vector Labs, Burlingame, Calif.) and viewed using a Nikon Eclipse TE2000 laser scanning confocal microscope (Nikon, Japan). The retinal flatmounts were probed with anti-NeuN, a marker for RGCs and some displaced amacrine cells.

RGC Imaging and Counts: Retinas were first imaged at 4× magnification and a grid was placed over each retina to randomly select 8 locations to be imaged at 40× magnification. The NeuN-labeled cells in each region were counted manually using ImageJ software and Metamorph®.

EPO enzyme-linked immuno-sorbant analysis (ELISA) and hematocrit: Serum from blood samples was probed for EPO using the human Quantikine® IVD® EPO ELISA Kit according to manufacturer's protocol. It should be noted that the ELISA kit is calibrated against human EPO and has been shown to be 4-fold less sensitive for rhesus versus human EPO. This was taken into account for calculations within this Example. The absorbance at 450 nm with a 600 nm reference was detected on a BioTek—8 µQuant® plate reader. In some mice the serum samples were pooled in order to obtain sufficient material for the ELISA. Hematocrit was measured by capillary centrifugation.

Optic nerve histology: Optic nerves were isolated and placed in 4% paraformaldehyde in 0.1 M phosphate buffer, pH 7.4 for one week at 4° C. Next, samples were post-fixed in 1% osmium tetroxide in 0.1 M cacodylate buffer, dehydrated in a graded ethanol series, further dehydrated in propylene oxide and embedded in Embed-812 resin (EMS, Hatfield Pa.), cut into 1 µm-thick sections and stained with 1% p-phenylenediamine in 50% methanol. Sections were viewed by light microscopy using an Olympus BX51 microscope. Prior to beginning axon counts, the optic nerve was traced at 20× magnification and cross-sectional area automatically calculated using ImageJ software. The entire length from top to bottom of same cross section was then imaged using a 60× oil immersion lens. Approximately the same region of 0.010 mm² was selected from each high magnification image; both live and dead axons were manually counted using ImageJ software. Measurements of the cross-sectional area of the optic nerve were used with axon density to estimate the total number of axons.

Statistical analysis: A one-way ANOVA followed by a pair-wise Bonferroni post hoc comparison test was used to determine statistical significance when comparing NeuN counts and axon counts. Statistical analysis was performed with Prism 4.0 software.

Results

Dose dependent increase in hematocrit and serum EPO-R76E levels: The left quadriceps of BALB/cByJ mice were injected with rAAV vector carrying either enhanced green fluorescent protein (eGFP, negative control), EPO (positive control), or EPOR76E. The amount of circulating EPO (including EPO-R76E) in each animal and the hematocrit was quantified (Table 5).

TABLE 5

Hematocrit and serum EPO levels in treated and control mice.

| Treatment | Hematocrit | EPO (mU/ml) | N |
|---|---|---|---|
| rAAV.CMV.eGFP | 46% ± 1.7 | 0 | 10 |
| rAAV.CMV.Epo | 84% ± 4.5 | 83 ± 26 | 8 |
| Dose 1 | 47% ± 3.0 | 9 ± 3.4 | 6 |
| Dose 2 | 48% ± 8.5 | 30 ± 4.6 | 18 |
| Dose 3 | 64% ± 11.0 | 132 ± 13 | 4 |
| Dose 4 | 67% ± 7.8 | 264 ± 17 | 11 |

The values for hematocrit are ± SD and the values for EPO concentration are ± SEM.
N = number of mice.

Negative control mice had no detectable circulating EPO and an average hematocrit of 46%. Positive control mice that received rAAV2/5.Epo had 83±26 mU/ml (±SD) of EPO in their serum and an expected increase in the hematocrit to 84%. Due to the short duration of the experiment no phlebotomy was required for the mice to survive to the experimental endpoint. Two different serotypes of rAAV.EpoR76E were used in the study. Serotype rAAV2/5 was injected at 3×10¹⁰ (dose 1) or 1×10¹¹ gc (dose 2), and serotype rAAV2/8 was injected at 5×10⁹ (dose 3) or 1×10¹² gc (dose 4). The resulting serum EPO-R76E concentrations are listed in Table 5 from lowest (dose 1) to highest (dose 4). Treatment with dose 1 yielded 9±3.4 mU/ml EPO-R76E in the serum, and the average hematocrit in these mice was 47%. Treatment with dose 2 produced 30±4.6 mU/ml EPO-R76E in the serum and an average hematocrit of 48%. Treatment with dose 3 generated 132±13 mU/ml EPO-R76E in the serum and a hematocrit of 64%. Finally, treatment with dose 4 resulted in 264±17 mU/ml EPO-R76E in the serum, and a hematocrit of 67%. Thus, four different concentrations of EPO-R76E were generated in the serum along with the positive and negative controls. The two highest doses of EPO-R76E induced a rise in hematocrit above normal levels. However, despite three times the level of the positive control (EPO-R76E) in the serum, the hematocrit was almost 20% lower in dose 4 mice than in the rAAV.Epo injected mice. These data demonstrate a significant attenuation of the erythropoietic activity in EPO-R76E.

Figure 8A:
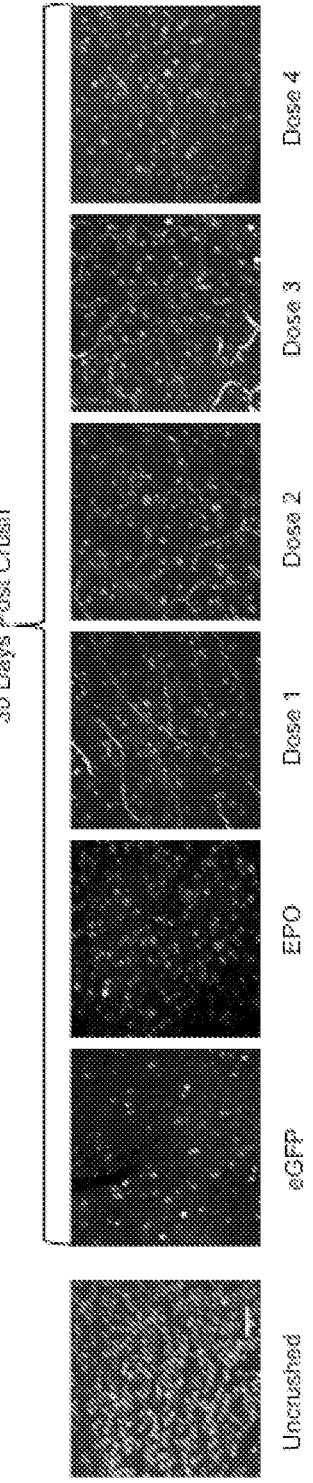
FIGS. 8A and 8B are digital images of micrographs and bar graphs showing that treatment with rAAV.CMV.Epo or rAAV.CMV.EpoR76E protects NeuN positive cells in the GCL layer against optic nerve crush.
Figure 8B:
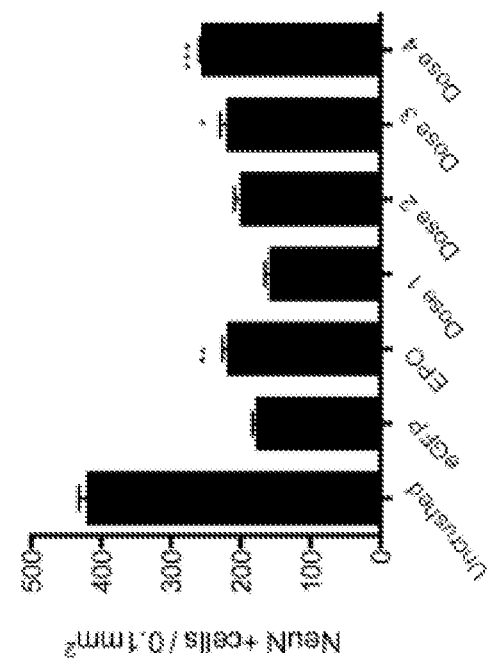

Systemic delivery of EPO-R76E protects NeuN positive cells in the ganglion cell layer in a dose dependent manner: Retinas from uninjected, normal mice had a high density of anti-Neuronal Nuclei (NeuN)-labeled cells in the ganglion cell layer (GCL) (FIG. 8A). As expected, after optic nerve crush there was a large decrease in the number of NeuN-labeled cells in negative control mice. Even in treated mice (EPO or Doses 1-4 of EPO-R76E) there were many fewer NeuN-positive cells in the GCL as compared to the no crush control. However, the retinas from mice treated with rAAV.Epo did appear to have more NeuN-labeled cells in the GCL after optic nerve crush than the retinas from mice treated with rAAV.eGFP. The number of NeuN-labeled cells also appeared to be higher in mice treated with either doses 3 or 4 of EPO-R76E as compared to the negative control group. In fact, retinas from mice treated with either dose 3 or 4 appeared to have a similar density of NeuN-labeled cells as was observed in positive control animals. To confirm these observations, NeuN-labeled cells in the GCL layer in each group were manually counted (FIG. 8B). The average cell density of negative control mice 30 days after optic nerve crush was 175±34 cells/0.1 mm2, a 58% reduction from normal retina (418±82 cells/0.1 mm2). Treatment with rAAV.Epo (84 mU/ml EPO) prevented 10% of the neuronal loss (217±40 cells/0.1 mm2, $p \leq 0.01$). The protection provided by EPO-R76E was concentration dependent. At the lowest concentration, dose 1, EPO-R76E was unable to prevent neuronal cell death (157±31 cells/0.1 mm2). Treatment with dose 2 of EPO-R76E increased the NeuN-positive cell density to 198±45 cells/0.1 mm2 (5% greater than the negative control). This level trended towards neuroprotection, but was not statistically significant. The two highest concentrations of EPO-R76E tested provided statistically significant protection using the stringent Bonferroni posthoc test. The NeuN-labeled cell density was 218±37 cells/0.1 mm2 ($p \leq 0.05$) and 253±25 cells/0.1 mm2 ($p \leq 0.001$), for doses 3 and 4, respectively. For Dose 3, this correlated to a 52% of no crush control levels (10% more than the negative control, and identical to treatment with rAAV2/5.Epo; FIG. 8B). Dose 4 of EPO-R76E resulted in 14% more NeuN-labeled cells than mice treated with the EPO vector ($p \leq 0.05$), a preservation of 60% of retinal ganglion cells (60% of no-crush control levels). These results demonstrate that neuroprotection by systemic EPOR76E is dose-dependent, and the two lowest doses were below the effective therapeutic concentration in this model.

Figure 9A:
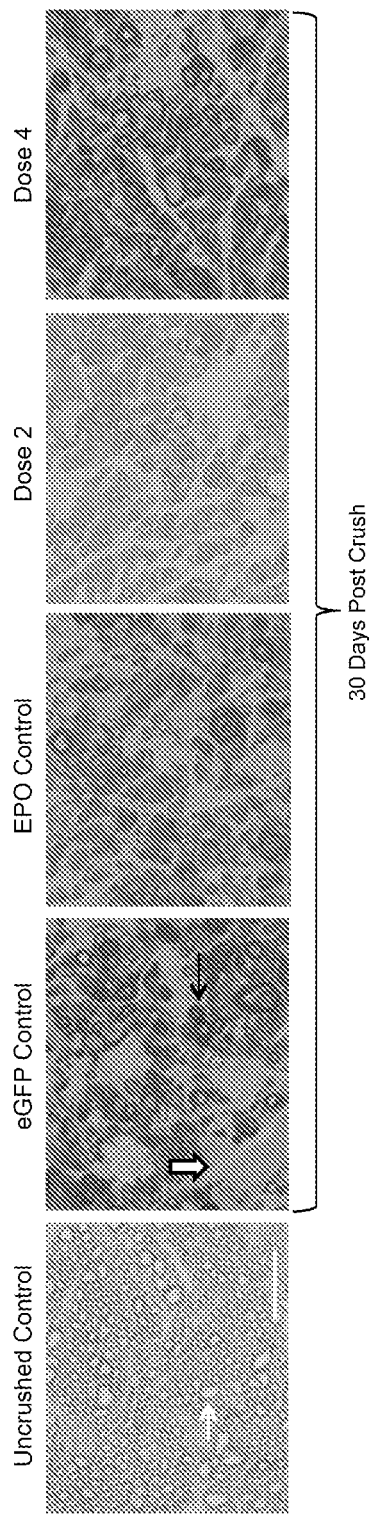
FIGS. 9A and 9B are digital images of micrographs and bar graphs showing that treatment with rAAV.CMV.Epo or rAAV.CMV.EpoR76E does not protect axons from optic nerve crush.
Figure 9B:
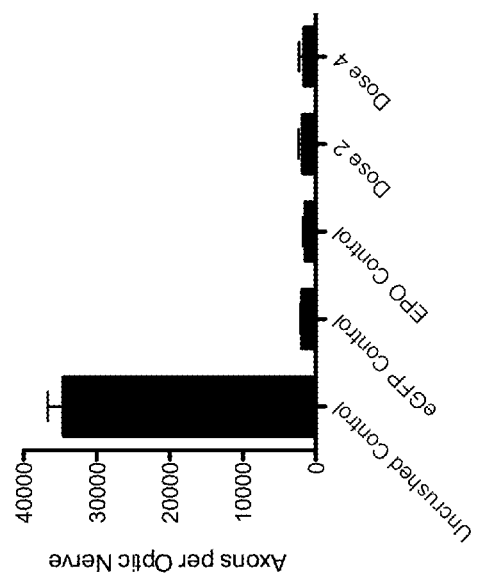

EPO is unable to protect axons in the optic nerve: p-Phenylenediamine was used to label myelin surrounding axons in the optic nerve. Stained cross sections of the nerves were examined by high magnification bright-field microscopy to determine the percentage of surviving axons in treated animals (FIG. 9A). The optic nerves from all mice that received an optic nerve crush, regardless if treated or controls, looked similar. They all had large areas of gliosis and many darkly labeled axons indicative of axonal degeneration. To confirm this observation, the myelinated axons with clear axoplasms were manually counted using a grid system (FIG. 9B). Cross sections from uncrushed optic nerves contained an average of 34,562 healthy axons with few if any dead axons. Following optic nerve crush this number decreased to 1,877 normal appearing axons per optic nerve in negative control mice, 1,452 normal appearing axons per optic nerve in positive control mice, and 1,808 normal appearing axons per optic nerve in mice that received Dose 4 of EPO-R76E. There was no statistically significant difference in the number of surviving axons in any of the optic nerve crush groups between any treatment or control conditions. All groups had a statistically significant decrease in the number of axons as compared to the no crush control.

Discussion

The mouse GCL is composed of nearly 60% displaced amacrine cells and 40% RGCs. In addition to labeling RGCs, NeuN also labels a small population of displaced amacrine cells (5-15%) in the GCL. Therefore, it is possible that the population of neurons being protected by EPO is composed of RGCs, displaced amacrine cells, or both. However, in rat, displaced amacrine cells are not affected one month after optic nerve lesion (see Kielczewski et al., *Invest. Ophthalmol. Vis. Sci.* 46, 3188-31962005), making it likely that EPO and EPOR76E are protecting RGCs only and not displaced amacrine cells.

Systemic EPO-R76E protects RGCs in a dose-dependent manner. At the lowest dose of EPO-R76E (9 mU/ml) there was no neuroprotection, at the second lowest dose (30 mU/ml), there appeared to be a trend towards neuroprotection but it was not significant using stringent statistical criterion. Significant protection of RGCs in the DBA/2J mouse model of glaucoma was detectable with 67 mU/ml EPO-R76E (see Example 2 and Sullivan et al., *J. Hum. Gene Ther.* 22, 1191-1200, 2011). In the current study, the third dose (132 mU/ml) caused a significant increase in the numbers of RGC surviving after ONC, and the treatment effect increased with the highest dose tested (264 mU/ml). But, even the highest dose of EPO-R76E only prevented 18% of the RGC death, indicating that there may be a more effective dose than those tested in this study. These results indicate that the low end of the therapeutic dose curve for EPO-R76E in this model lies between 30 and 67 mU/ml. The correlative increase in hematocrit levels precluded assessment of higher doses of systemic EPO-R76E. The neuroprotective effect of EPO is well characterized in RGCs and is similar to that observed in other neurons (see Kretz et al., *Mol. Cell. Neurosci.* 29, 569-579, 2005; Weishaupt et al., *Invest. Ophthalmol. Vis. Sci.* 45, 1514-1522, 2004; Zhong et al., *Invest. Ophthalmol. Vis. Sci.* 48, 1212-1218, 2007; King et al., *Mol. Cell Neurosci.* 29, 569-579, 2007). Following injury of the optic nerve RGC cell bodies die by apoptosis, characterized by activation of caspases 3 and 9, downregulation of PI-3K/Akt kinases, degradation of nuclear DNA and condensation of the nuclei. EPO blocks apoptosis preventing death by blocking the activation of caspase 3 through the PI-3-Kinase, Akt pathway (Weishaupt et al., 2004), and by upregulating Bcl-XL (Kretz et al., 2005). The findings of the present study do not contradict these findings and in fact support them as a potential mechanism.

Conclusion

Obtaining the optimal therapeutic dose is critical for any drug delivery, maximizing the wanted effect of the agent and minimizing negative side effects. To be effective as a neuroprotectant EPO must be administered at levels higher than is approved for treatment of anemia in humans (for review see, Ehlers, *Trends Neurosci.* 27, 3-6, 2004). EPO, like many other cytokines, may have a bell shaped dose curve, making it difficult to define the optimal therapeutic dose (Weishaupt et al., 2004; Zhong et al., 2007). As disclosed herein the identify the lower limit was identified for circulating EPO required for neuroprotection of RGCs, with the threshold of statistically significant neuroprotection being greater than 30 mU/ml EPO-R76E in the serum. Further protection of the RGCs was achieved by treatment with higher doses and it is possible that we have not detected the peak effect since the highest dose tested still showed improved protection of RGCs. Unfortunately, the two highest doses of continuous, systemic EPO-R76E (132 and 264 mU/ml), raised the hematocrit to levels that would not be acceptable in humans (65-67%). The promise of EPO-R76E for neuroprotection warrants its examination as a treatment for many neurodegenerative diseases, such as: glaucoma, Alzheimer's disease, Parkinson's Disease, spinal cord injury, and even neurotrauma.

Example 4

Methods and Materials

VMD2.rtTA:rds/rds mice: The VMD2.rtTA mice were acquired from Johns Hopkins University, Baltimore, Md., and the rds/rds mice were acquired from Jackson Laboratories. The VMD2.rtTA mice were crossed to the rds/rds mice for 8 generations. Mice were genotyped by PCR for the presence of VMD2.rtTA and the 10 kb insertion into the peripherin/rds gene.

Generation of rAAV Plasmid #401: rAAV2/1.epoR76E.tet.egfp. The final titer was $1.4 \times 10^9$ gc/mL Subretinal Injections: Five to seven day old VMD2.rtTA:rds/rds mice were bilaterally injected into the subretinal space. Mice were injected with 2 μL of $1.4 \times 10^9$ gc/mL rAAV2/1.epoR76E.tet.egfp into the subretinal space using a blunt 10 μL, 30 gauge Hamilton syringe.

Doxycycline treatment: VMD2.rtTA:rds mice were weaned at PD21 and given an intraperitoneal (IP) injection of 200 μL of 4 mg/mL doxycycline in 0.1M sodium phosphate buffer (equal to 800 μg). Mice were then treated with 0, 0.5, or 5 mg/mL doxycycline continuously from PD22 to PD60. Five percent sucrose was added to the doxycycline containing water. Water was changed every 2-3 days. Control mice received only the subretinal injection of vector.

OCT: Ultra-High Resolution Spectral Domain Optical Coherence Tomography (OCT; Bioptigen, Durham, N.C.) of the retina was performed on VMD2.rtTA:rds/rds mice at PD60. Mice were anesthetized with ketamine/xylazine, eyes were dilated with 1% tropicamide and moistened with Systane Ultra. Each mouse was wrapped in gauze, placed in a mouse holder and imaged with a mouse retina bore.

ELISA Eyes were collected in 100 μL of specimen diluent, homogenized and sonicated, then run in duplicate on a Human Erythropoietin Platinum ELISA kit according to manufacturer protocol (eBioscience, San Diego, Calif.). The plate was read on a MicroQuant plate reader (BioTek, Winooski, Vt.) at 450 nm with a 620 nm reference.

Histology: Mice were euthanized by overdose of ketamine/xylazine and cervical dislocation. Before enucleation, a small area of the cornea on the nasal side was cauterized for orientation of the eye during embedding. Eyes were preserved in 4% paraformaldehyde overnight at 4° C., then cryo-protected in 30% sucrose solution overnight at 4° C. Eyes were embedded in Tissue Freezing Medium (Triangle Biomedical Sciences, Inc., Durham, N.C.) and stored at −80° C. Ten micron cross sections of the eye were collected in round so that each slide contained representative sections through the entire eye. Sections were stained with Hematoxylin and Eosin and imaged on a Nikon Eclipse 80i microscope (Tokyo, Japan). The NIS Elements Version 3.0 (Nikon, Tokyo, Japan) program was used to measure the outer nuclear layer thickness every 0.5 mm on both sides of the retina starting from the optic nerve head.

Results

Figure 10:
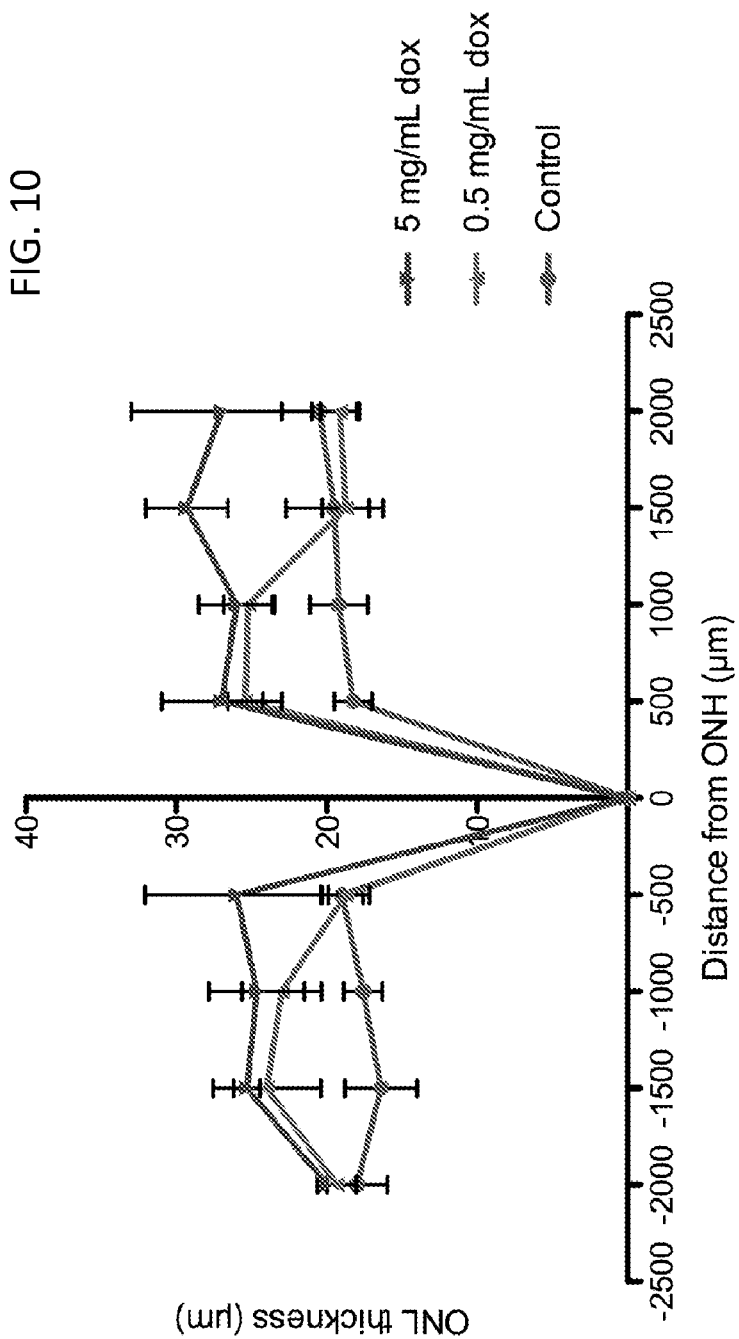
FIG. 10 is a graph of outer nuclear layer thickness in rds/rds mice treated with a subretinal injection of rAAV.tet.EpoR76E followed with either 0.5 or 5 mg/ml dox water. Protection of photoreceptors was achieved by intraocular delivery of EPO-R76E.

EPO ELISA An average of 5.2 mU/ml EPO was detected in the control eyes of mice that did not receive dox. Mice that received a single IP injection of dox (equal to 800 μg dox), but no dox water contained, 7.8 mU/mL intraocular EPO. Mice that received 0.5 or 5 mg/mL dox water, had 23.1 mU/mL or 36.5 mU/mL intraocular EPO, respectively (FIG. 10).

Concentration of Dox Consumed: The results were normalized to the volume of water consumed per mouse. As the dose of doxycycline increased, the amount consumed decreased, presumably because of the bitter taste of the water despite the addition of sucrose. The 10 fold increase in doxycycline from 0.5 to 5 mg/mL resulted in a 6.5 fold increase in the amount of doxycycline consumed per mouse per day (3.9 to 25.5 mg).

Figure 11:
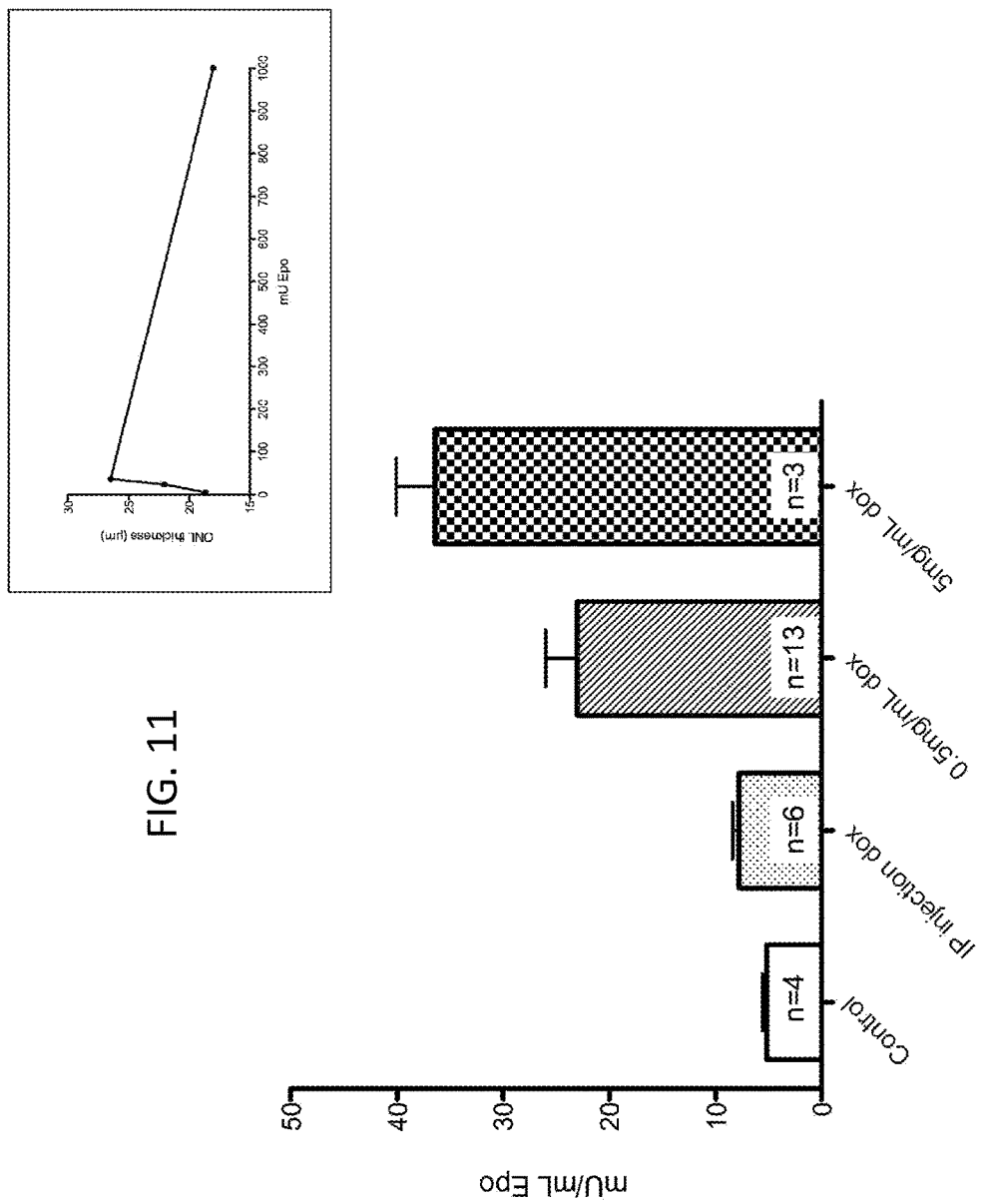
FIG. 11 is set of graphs showing the amount of EPO-R76E in the eye after subretinal injection of rAAV.tet.EpoR76E and treatment with 0, 0.5, or 5 mg/ml dox water. Treatment with a single IP injection of dox at weaning resulted in about 8 mU/ml EPO in the eye and no neuroprotection. Treatment with 0.5 or 5 mg/ml dox yielded 25 and 36 mU/ml EPO-R76E in the eye, respectively. The inset line graph correlates intraocular EPO-R76E levels with photoreceptor protection. Protection was achieved at 25 and 36 mU/ml, but not at 8 or 1000 mU/ml EPO-R76E in the eye.

Histology verifies that low levels of EPO are neuroprotective to photoreceptors: The outer nuclear layer (ONL) thickness was measured every 0.5 mm from the optic nerve head moving inferior to nasal. ONL thickness increased as the doxycycline concentration increased (FIG. 11).The average thickness at 0.5 mm from the optic nerve head was: 18.63 μm±1.33, X μm±X, 22.1 μm±1.38, and 26.5 μm±5.04 for the negative control, single IP injection, 0.5 mg/mL dox, and 5 mg/mL dox treatment groups, respectively. *Or . . . The average thickness at 0.5 mm from the optic nerve head was: 18.63 μm (SEM=1.33) for negative controls, X μm (SEM=X) for the single IP injection group, 22.1 μm (SEM=1.38) for 0.5 mg/mL dox, and 26.5 μm (SEM=5.04) for 5 mg/mL dox treatment group.

Example 5

Parkinsons disease is the second-most common neurodegenerative disorder, characterized neuropathologically by gradual degeneration of dopaminergic neurons in the substantia nigra. Behavioral symptoms include bradykinesia, akinesia, tremor, postural instability, and impaired function on "executive" tasks that involve planning, judgment, sustained attention, and other fronto-striatally-mediated cognitive processes. Currently there is no cure for Parkinson's disease, and current interventions are typically directed toward diminishing behavioral symptoms and enhancing quality of life. The most commonly-used treatments at the moment are only partially and transiently effective, or are only effective in a minority of patients. Importantly, they do not address the most insidious feature the disorder, namely the progressive destruction of nigro-striatal neurons.

1-methyl-4-phenyl-1,2,3,6-tetrahydropyridine (MPTP) has been used extensively to model Parkinson's disease in species as diverse as monkeys, mice, and worms. Injected systemically, it destroys dopaminergic neurons rapidly and reliably. MPTP readily enters the brain and is converted to the toxic metabolite 1-methyl-4-phenylpyridinium (MPP+) by monoamine oxidase (MAO). MPP+ is then taken up by the dopamine transporter where it depletes vesicular dopamine and inhibits complex I mitochondrial respiration, ultimately resulting in the neuronal death. In monkeys MPTP produces a profound akinesia and tremor; however in mice Parkinson-like behavioral consequences are typically minimal and transient, even at large doses.

Erythropoietin (EPO) is a glycoprotein responsible for generating red blood cells. The volume of blood occupied by red blood cells, or hematocrit, is tightly controlled at 40-45% by an Epo-mediated feedback loop. It has long been known that EPO is neuroprotective; however, long-term systemic administration raises hematocrit to unacceptably high levels and may be fatal. Intracranial administration is an alternative but requires surgery. Genc et al. (2001) showed that Epo can protect against MPTP neurotoxicity. They injected wild-type Epo directly into the substantia nigra of mice either 24 hours before or immediately after MPTP, and found that in both cases Epo prevented the hypokinesia associated with subchronic MPTP. Similarly, Puskovic et al. (2006) showed that HSV-mediated native EPO injected intra-striatally a week before MPTP injections prevented dopaminergic loss. These studies demonstrate proof-in-principle that the neuroprotective properties of Epo are effective against MPTP-induced neurotoxicity. Indeed, Wu et al. (2010) showed a region-specific upregulation of Epo receptors in the substantia nigra following 5 daily injections of 30 mg/kg MPTP.

As disclosed herein, the disclosed novel EPO variants designed to retain their neuroprotective properties without raising hematocrit. One of them has shown effectiveness in mouse models of retinal degeneration and glaucoma, but prior to this disclosure it was not known whether it will be effective in a model of neurodegeneration in the brain.

Methods

Subjects: Subjects were 9-month-old male wild-type C57BL/6J mice from Jackson Laboratories (Bar Harbor, Me.). Mice were housed 5 per cage in tub cages under standard conditions in AALAC-approved vivarium, except for the 5 days during and 5 days following the MPTP injection regimen as described below. Mice had free access to food and water for the duration of the study.

Generation and administration of rAAV vectors: EpoR76E and EpoS71E were produced by site-directed mutagenesis of rhesus EPO (ARIAD pharmaceuticals) using the Quickchange multi-site kit according to manufacturer's protocol (Stratagene). Two nucleotides were altered to result in a conversion of arginine at position 76 to a glutamate for EpoR76E and a serine to a glutamate at position 71 for EpoS71E. The sequences were subcloned into an AAV2 backbone plasmid The rAAV was isolated and purified from the cells by double cesium chloride gradient centrifugation and dialyzed in HEPES-buffered saline (pH7.8), and the viral titer was determined using the LightCycler 480 real-time quantitative PCR machine (Roche) and primers specific to the polyA tail. The rAAV vectors were administered in the gastrocnemius muscle by microsyringe (Hamilton) in a volume of 10 μl (1.0×1011 genome copies).

1-methyl-4-phenyl-1,2,3,6-tetrahydropyridine (MPTP): MPTP HCl (#M0896, lot #48K1861), Sigma) was dissolved in physiological (0.9%) saline at a concentration of 1.8 mg/ml free base (2.11 mg/ml salt). Starting 3 weeks after injection of the rAAV constructs, mice were given one injection of MPTP saline per day for 5 consecutive days. Injections were given subcutaneously at a volume of 10 ml/kg to achieve a dose of 18 mg/kg. A 30 mg/kg dose was used initially, the standard dose with the subchronic regimen. However, this dose proved fatal to a large number of mice of this age so it was reduced to 18 mg/kg. While receiving MPTP injections, mice were housed in disposable cages under a fume hood to protect personnel from aeration of the toxic MPP+ metabolite excreted in the urine and feces. The cages remained under the hood for 5 days after the last injection, when mice were transferred to clean tub cages and returned to the vivarium.

Locomotor activity: Locomotor activity was assessed in 60-min. sessions in commercially-available activity monitors (MED-Associates). The activity monitors measured 27×27 cm, with 16 infrared beams equally spaced in the x and y axes of the horizontal plane, 1 cm from the floor of the monitor. An additional vector of 16 photobeams was situated 5 cm above the floor to track rearing. Mice were placed in the activity monitors for a 30-min. session before receiving MPTP, and matched on activity levels for assignment to MPTP or saline groups, with the constraint that every subject within a cage was required to receive either MPTP or saline for biosafety reasons. Following MPTP mice were given an additional 60-min. session in the activity monitors.

Sensorimotor function: A number of tasks were conducted to measure balance, coordination, including rotorod, horizontal beam, rope climb, block test, inverted screen, vertical pole, grid test, and sticker test. Balance and coordination were assessed using a Rotamex-5 rotorod (Columbus Instruments). After a single practice trial, mice were trained for three trials per day for 3 consecutive days to balance on a rotating rod 3 cm in diameter. The rotation speed increased from 0 to 80 RPM, incrementing 0.8 rpm every 3 s. If a mouse fell within 15 s it was given a second opportunity. In some cases mice would grasp the rod and rotate around with it. in this case the time at which the first rotation occurred was noted, and latency to fall or to the first rotation was the measure of interest. The horizontal beam task required the mouse to traverse a 0.64-cm diam., 80-cm long beam elevated 40 cm above a blanket. Mice were motivated by a 25-watt white light bulb at the starting platform, and reinforced with entry into a dark box on the other side of the beam. Mice were placed on the 5-cm$^2$ starting platform, and latency to initiate (all four paws on the beam), latency to traverse, and number of paw slips were recorded. The rope climb involved a similar avoidance of a 25-watt white light bulb and escape into a dark box. Mice were placed on the 1.5-cm-diam. rope facing down to start the trial. Latency to turn around and latency to climb the 25 cm into the dark box were recorded. On the block test, the mouse was placed on a block, 10 cm 2 and 3 cm high. The latency to put its forepaws, and then all four paws on the table were recorded. A second version was used in which the mouse was placed on the table with its forepaws on the block, and the latency to move the forepaws to the table was recorded. On the inverted screen task mice were confined to a 15-cm$^2$ section of 1-cm$^2$ hardware cloth. The screen was waved in the air several times to induce a gripping response, and then inverted. The duration to fall was recorded with a maximum of 60 s. On the vertical pole task mice were placed on top of a 2.5-cm diam. polystyrene ball situated top a 40-cm-long pole covered in Self-Grip athletic tape (98% cotton, 2% latex). The pole was rooted in a sling and mounted in a cage containing clean bedding. The latency to come of the ball and place all four paws on the pole, and the latency to climb down the pole and place all four paws on the bedding were recorded. On the grid task the subject was placed on a screen of 1-cm$^2$ hardware cloth situated vertically. The latency to move all four paws was recorded. On the sticker test a small round sticker was placed on the mouse's snout and the mouse was placed in a clean tub cage free to move about. The latency to the first attempt to remove the sticker was recorded, as well as the latency to remove the sticker.

Tremor: Tremor was assessed using a force-plate actometer (FPA; BASi). The FPA consisted of a 44-cm2 carbon fiber load plate situated on four force transducers, one at each corner, within a ventilated sound-attenuating cubicle illuminated by an 8-watt fluorescent bulb. The position of the subject was tracked by the relative force impinging of each of the transducers, producing measures such as horizontal locomotor activity, stereotypy, and bouts of low activity. With spatial resolution of 1 mm and temporal resolution of 1 msec, the FPA tracks variations in power to quantify tremors ranging from 0.1 to 24.6 Hz. Mice were placed individually in the FPA enclosure for a period of 5 min. and then removed to their home cages. The apparatus was cleaned with 15% ethanol after each session.

Histology and immunohistochemistry: Mice were sacrificed 5 weeks following the last MPTP injection. Mice whose brains were used for immunohistochemistry were perfused transcardially under isoflurane anesthesia, first with ice cold saline and then with 4% paraformaldehyde in 0.1 M PBS (pH 7.4) for 30 min. Brains were removed and fixed overnight in the same fixative, cryo-protected, and then 40-μm coronal cryostat sections were taken throughout the extent of the substantia nigra and striatum for histological analysis. Free-floating sections were treated first with phosphate buffered saline (PBS) containing 20% methanol and 3% hydrogen peroxide for 30 min., and rinsed thoroughly in PBS. Sections were then incubated in 10% normal horse serum in PBS containing 0.1% Triton X-100 for 30 min. and incubated overnight at 4° C. in the primary antibody (dilution 1:200) targeting tyrosine hydroxylase (TH; #AB152, Millipore). Following incubation sections were rinsed three times in PBS, incubated for an hour in a biotinylated anti-rabbit IgG (Vector Labs), washed thrice, and treated with avidin-biotin complex (Vectastain Elite ABC kit, Vector Labs) reagent for an hour and visualized using diaminobenzidine. Sections were then mounted on slides and air-dried. Some sections were incubated in the anti-TH primary antibody and processed with a fluorescent donkey anti-rabbit secondary antibody (FITC, Vector Labs). Optical density of TH-positive fibers in the striatum were quantified from 2-6 greyscale sections per subject using the public domain software ImageJ (http://rsb.info.nih.gov/ij). Fluorescent images of striatal TH-positive fibers were captured using a Zeiss 710 confocal microscope.

HPLC with electrochemical detection: Mice whose brains were used for HPLC were sacrificed by cervical dislocation without anesthesia, and trunk blood collected for measurement of hematocrit. Brains were dissected rapidly and punches 1 mm in diam were taken from the dorsal striatum of 2-mm thick coronal sections and flash-frozen in liquid nitrogen. The frozen striatal punches were suspended in 400 μl aCSF and 600 μl 0.2 mM perchloric acid, homogenized for 30 sec., and then centrifuged at 10,000 RPM for 15 min at 4° C. The supernatant was filtered through a nylon syringe filter (0.2 μm) and frozen at −80° C. Frozen samples (10 μl) were automatically injected by a CMA 200 refrigerated autosampler (CMA Microdialysis) onto a 150±2 mm ODS C18 column (ESA Inc.) connected to an ESA model 580 HPLC pump. The mobile phase, containing 80 mM sodium dihydrogen phosphate monohydrate, 2.0 mM 1-octanesulfonic acid sodium salt, 100 μl/l-triethylamine, 5 nM EDTA, and 10% acetonitrile, pH 3.0, was perfused at 0.25 ml/min. Dopamine levels were determined using an ESA 5041 high-sensitivity analytical cell, an ESA 5020 guard cell, and an ESA Coulochem II 5200A electrochemical detector. The guard cell was set at +350 mV with the analytical cell set at a potential of +220 mV and the current gain at 1 nA. Under these conditions, the limit of detection for DA is 100 fg per injection.

Stereological quantification of cells in SNc: For unbiased stereological quantification of TH-positive cells, every eighth section through the rostro-caudal extent of the SNc was measured using the optical fractionator counting method and Stereo Investigator software (MicroBrightField) in the Neuroscience Institute's Imaging Center at UTHSC: The contour of the SNc was first delineated using Stereo Investigator's anatomical mapping tool at low power. TH-positive cells within the SNc were counted in from 10 to 20 frames measuring 25×25 μm in each of the selected sections, generated using Stereo Investigator's random sampling grid. The frames were selected using the systematic random sampling scheme, which provides an unbiased and efficient sampling technique. In every counting-frame location, the top of the section was identified, after which the plane of the focus was moved 4 μm deeper through the section (guard zone) to prevent counting inaccuracies due to uneven section surfaces. The resulting focal plane served as the first point of the counting process. All TH-positive cells that came into focus in the next 8-μm segment (dissector height) were counted if they were entirely within the counting frame or touching the upper or right side of the counting frame. Based on the these parameters and counts, the total number of TH-positive cells per selected region were counted using the optical fractionator formula N=1/ssf×1/asf×1/hsf×Q, where ssf is the section sampling fraction, asf is the area sampling fraction, hsf is the height sampling fraction (dissector height divided by the section thickness after shrinkage), and Q denotes the total count of particles sampled for each region.

Data analysis: Most behavioral, histological, and neurochemical data were analyzed using orthogonal paired comparisons or orthogonal polynomials. Time-series data were analyzed using hierarchical linear modeling, with time as an unbalanced continuous numerical repeated measure and subject as a random factor nested within treatment group and genotype. Degrees of freedom on repeated-measures analyses were corrected for variations in sphericity using Huynh-Feldt ε. To protect against spurious Type I errors, follow-up analyses were conducted only after a significant omnibus effect, except for comparisons having specific a priori hypotheses. All statistical tests were two-tailed with α=0.05.

Results

Figure 12:
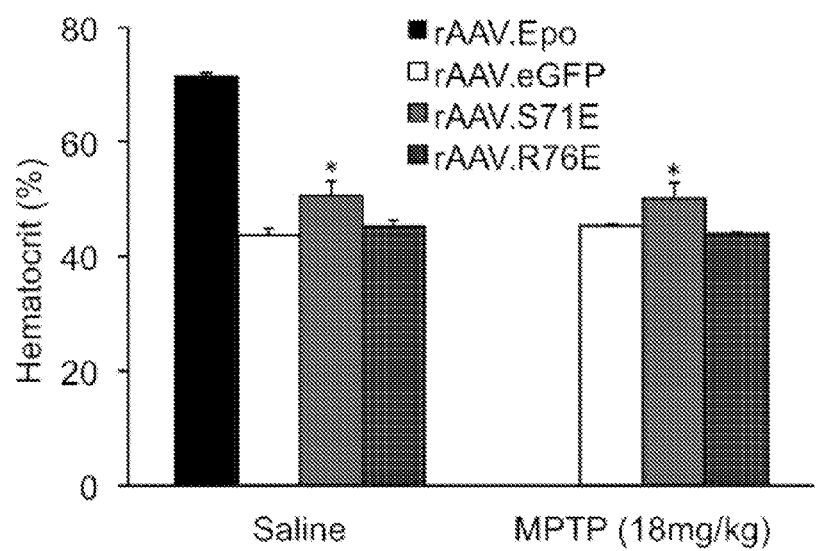
FIG. 12 is a bar graph showing that modified EPO constructs are nonerythropoietic. Mice were injected intramuscularly with an rAAV vector harboring native Epo, eGFP control, or modified variants EpoR76E or EpoS71E. Trunk blood was collected 3 weeks following the injection and hematocrit measured. Most of the mice injected with rAAV.Epo died; those that survived had significantly elevated hematocrit levels. Mice injected with rAAV.eGFP or rAAV.EpoR76E had normal hematocrit levels. In the rAAV.EpoS71E group had slightly (13.9%±4.0%) elevated hematocrit that was statistically significant.

Five weeks following the first MPTP injection, mice were sacrificed and brains processed for immunohistochemistry or HPLC. Trunk blood was collected and hematocrit was measured in experimental mice, as well as a positive control group receiving native Epo (rAAV.Epo) and given five daily injections of saline. Most of the mice in this positive control group died, but those that survived had elevated hematocrit (71.5±0.5%; FIG. 12) compared to the normal range for male mice of 44-48% and exemplified by the rAAV.eGFP negative control group. Hematocrit levels were slightly but significantly elevated (50.3±2.7%) in mice pre-treated with rAAV.EpoS71E compared to rAAV.eGFP controls [t(20)=3.2, p=0.0037], although nowhere near the native EPO levels. Hematocrit levels were in the normal range for rAAV.EpoR76E]treated mice. There was no effect of MPTP on hematocrit [t(20)=0.02, p=0.981].

Figure 13A:
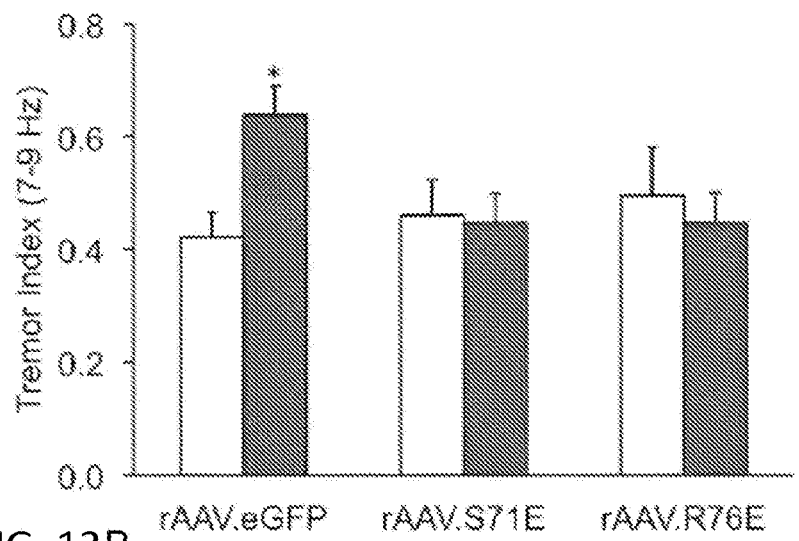
FIGS. 13A and 13B are bar graphs showing that modified EPO variants protect against MPTP-induced parkinsonism.
Figure 13B:
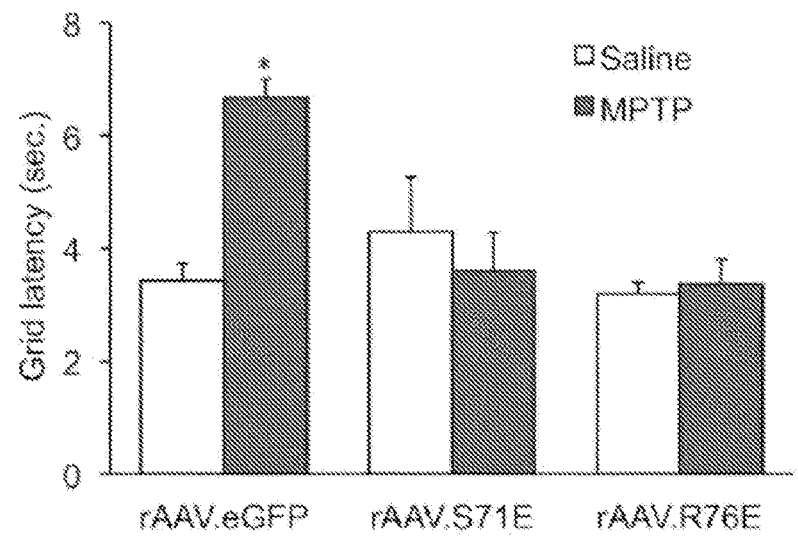

Although mice do not exhibit the robust behavioral deficits observed in monkeys after MPTP lesioning, subtle behavioral changes are often observed with the subchronic regimen using the standard 30 mg/kg dose. However, with a smaller dose little in the way of behavioral changes were seen. There were no effects of lesion or treatment on any of the measures in the activity monitors. Similarly, most of the sensorimotor tasks were unaffected by MPTP. However, MPTP induced a significant tremor in the 7-9 Hz range, in mice pre-treated with rAAV.eGFP [FIG. 13A; t(29)=2.3, p=0.0268]. MPTP did not affect tremor in either of the modified EPO groups [t's<0.6, p's>0.592]. There was also significant effect of MPTP on the grid task (FIG. 13B). When first placed on the grid, mice normally adapt quickly and move all four paws within 3-4 seconds, as exemplified by saline control mice in all treatment groups. However, MPTP-lesioned mice took twice as long to start moving as regular mice when pre-treated with rAAV.eGFP, indicative of akinesia [t(28)=3.2, p=0.0037]. When pre-treated with either of the modified EPO constructs, MPTP did not significantly affect grid movement latencies grid movement latencies [t's<0.8, p's>0.436].

Figure 14:
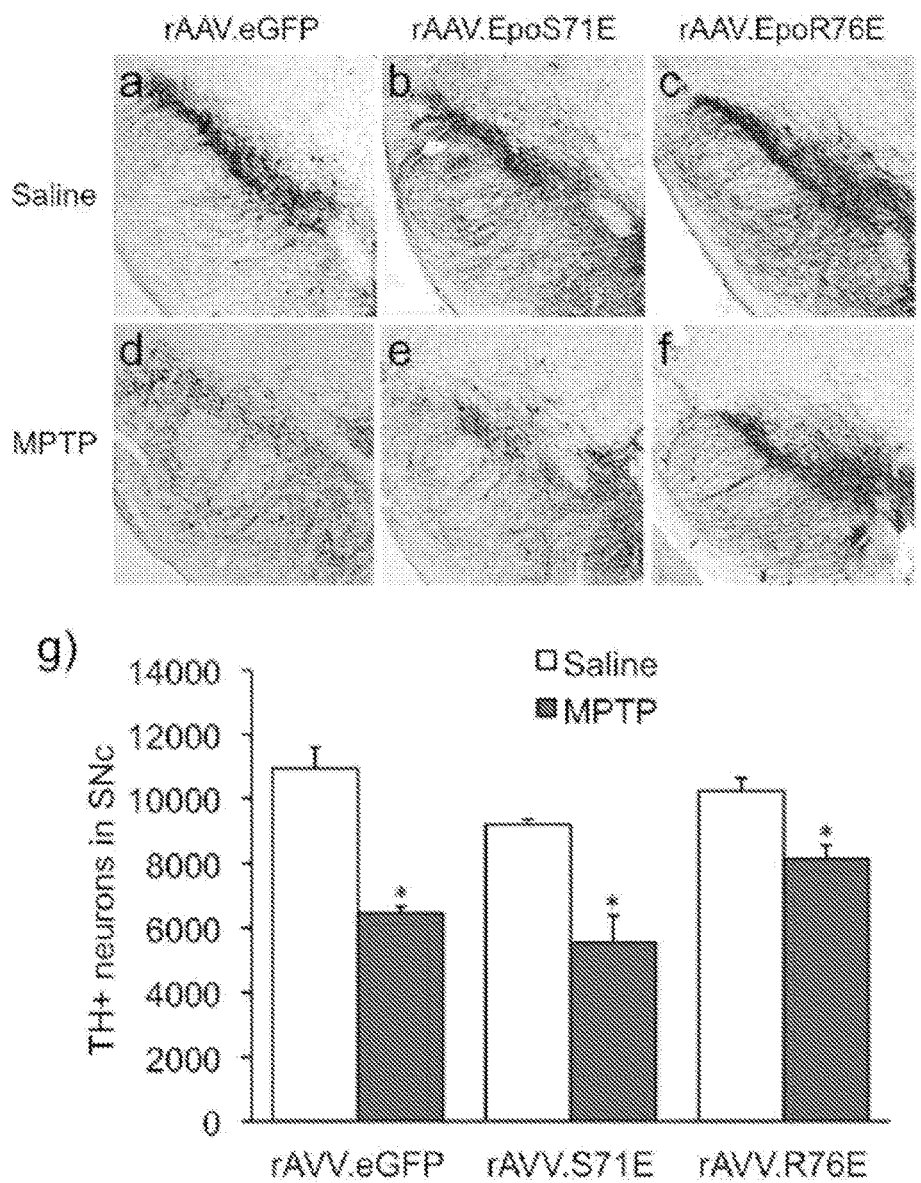
FIGS. 14A-14G. rAAV.EpoR76E protects against MPTP-induced destruction of neurons in the SNc.

FIG. 14 shows that five daily injections of 18 mg/kg MPTP induced significant damage to the SNc, inducing a 41.0% loss of TH+ neurons in mice pre-treated with rAAV.eGFP, compared to saline-injected controls [t(12)=5.3, p=0.0002]. The S71E EPO mutation did not protect nigral neurons, as these mice experienced a similar loss of 39.6% [t(12)=4.3, p=0.0010]. In contrast, nigral damage was only half in mice pre-treated with rAAV.R76E, compared to rAAV.eGFP control [20.4%; p=0.0302].

Figure 15A:
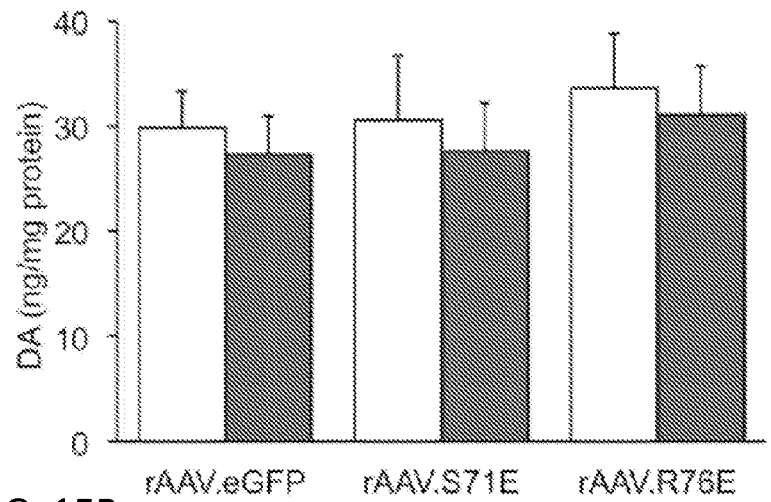
FIGS. 15A and 15B. Modified Epo variants normalize dopamine turnover following MPTP lesion.
Figure 15B:
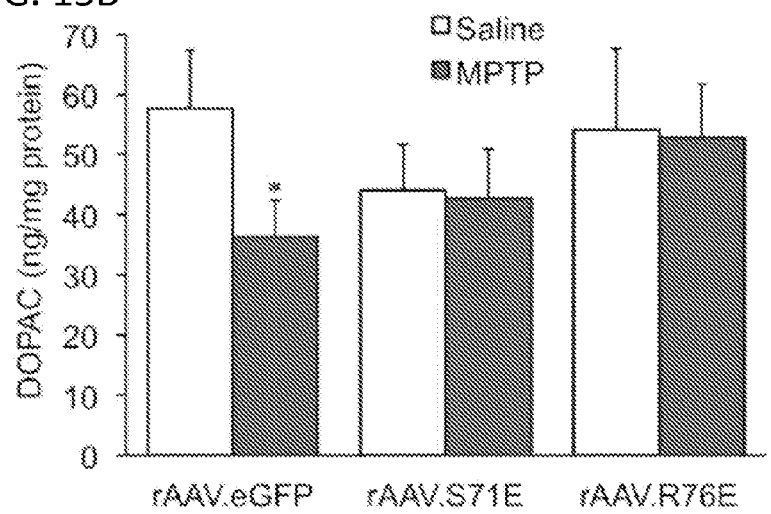

The effects of MPTP on striatal dopamine were not significant in any of the treatment groups (FIG. 15A; t's<1.38; p's>0.175). This may reflect the well-established effect of sprouting and re-innervation of dopaminergic neurons when mice are sac'd many weeks following MPTP lesions. In contrast, DOPAC was reduced only in the rAAV.eGFP control group FIG. 15B; [t(42)=2.15, p=0.0370]. This loss in DOPAC reflects a decrease in dopamine turnover of 30.1% in the rAAV.eGFP-treated control mice. In contrast, DOPAC did not change significantly (t's<0.14, p's>0.896) and turnover increased slightly in the rAAV.EpoS71E (1.4%) and rAAV.EpoR76E (6.2%) groups.

Figure 16:
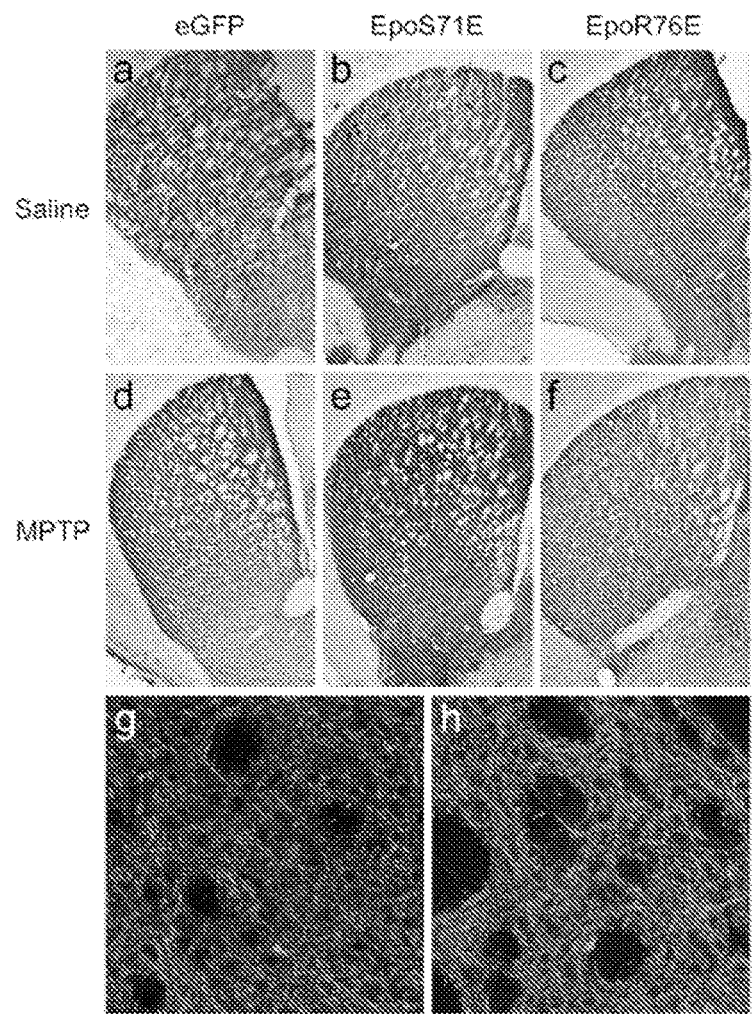
FIGS. 16A-16I. rAAV.EpoS71E pre-treatment increases TH-positive fiber density following MPTP lesion.
Figure 16:
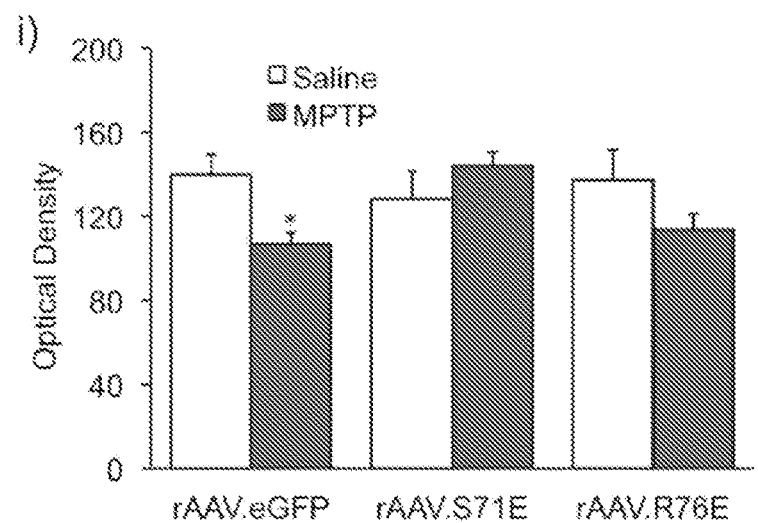

To investigate the reason for normal dopaminergic tone and lack of parkinsonism in rAAV.EpoS71E-treated mice despite a robust SNc lesion, TH-positive fibers were assessed in the striatum for possible differences in sprouting and regeneration. FIG. 16 shows that TH-positive fibers were significantly reduced (−23.7±3.9%) in the rAAV.eGFP control mice lesioned with MPTP, consistent with the SNc lesion observed in FIG. 4 [t(15)=2.51, p=0.0250]. A smaller, non-significant loss of TH-positive fibers (−17.4±5.6%) was observed in mice pre-treated with rAAV.EpoR76E (p=0.119). In contrast, density of TH-reactive fibers in MPTP-lesioned mice treated with rAAV.EpoS71E had normalized to that of their saline-treated counterparts (+12.1±5.4%) by the time they were sac'd (p=0.284).

Discussion

Disclosed herein for the first time, it is demonstrated that peripherally-administered nonerythropoietic erythropoietin can be neuroprotective in a model of a neurodegeneration in the brain. A relatively low dose of MPTP destroyed 41.0% of the dopaminergic neurons in the substantia nigra in control mice. When a single intramuscular injection of the EpoR76E construct was injected 3 weeks before the MPTP regimen, the lesion was less than half that size. The EpoS71E construct did not protect against MPTP-induced nigral cell loss, but enhanced sprouting of TH-positive fibers following the lesion. Thus by two different mechanisms, modified EPO constructs were able to maintain and/or restore good dopaminergic tone in MPTP-lesioned mice. The good dopaminergic function was reflected in protection from MPTP-induced parkinsonism. Taken together these results indicate that non-erythropoietic EPO delivered by viral vector is a viable therapeutic approach for CNS neurodegenerative disorders.

It has long been known that EPO is neuroprotective, and that its neuroprotective properties are independent of its effects on erythropoiesis. Rex et al. (2009) showed that direct delivery of erythropoietin to the retina in 7-day-old mouse pups prevents retinal degeneration (rd) in mice homozygous for a mutant Pde6brd allele, which are normally completely blind by weaning. They followed up this study by showing that two mutant EPO variants, including EpoR76E, were protective in the same rd model when packaged in an rAAV2/5.CMV vector and delivered intramuscularly (see Example 1 above). Intraocular delivery of the rAAV.EpoR76E construct also spared retinal ganglion cells from degeneration in a model of glaucoma (see Example 2 above). The EpoR76E variant was not fully protective in the MPTP model in the present study. However, MPTP administration is not the slow, natural degenerative process that characterizes the glaucoma and rd models. Rather, it is more of a "sledgehammer" effect, re-capitulating in 5 days the nigro-striatal damage that occurs over decades in Parkinson's disease. It is plausible that the EpoR76E construct may be fully protective in a model of slow CNS neurodegeneration. Despite only half the neuroprotection, EpoR76E-treated mice were fully protected from MPTP-induced tremor and akinesia. Consistent with this, dopamine and DOPAC levels in these mice were not significantly different from their saline-treated counterparts. This is not surprising given that large depletions of striatal dopamine are typically needed to observe parkinsonism in mice. Similarly, extensive nigro-striatal damage is thought to be needed in Parkinson's disease before symptoms are observable. The mechanism of EPO's neuroprotective effect has not been elucidated completely, but converging evidence suggests that it activates the PI3K/Akt components of the RISK pathway to increase the mitochondrial transmembrane potential ($\Delta\psi$mGiven that MPTP acts to inhibit mitochondrial respiration and decrease $\Delta\psi$m, it is likely this mechanism that protected half the striatal neurons from destruction by MPTP in the EpoR76E-treated mice.

In contrast to the partial neuroprotection observed in EpoR76E-treated mice, the MPTP lesion in the EpoS71E group was equivalent to that of the eGFP controls. However, like those in the EpoR76E group, mice pre-treated with EpoS71E did not exhibit parkinsonism. The recovery of dopaminergic tone and associated function after MPTP lesion is well-established, and is related to generation of new TH-positive fibers on surviving. In one study, mice were given four injections of 20 mg/kg spaced 2 hours apart. This acute regimen produces rapid necrotic neuronal death and near-complete depletion of striatal dopamine that recovers over time. They sac'd mice at several time points following MPTP administration, 24 days being the longest. They found that sprouting of new TH-positive fibers started almost immediately after MPTP lesion, was time-dependent, and was accompanied by increased intracellular dopamine content in striatal punches. After 24 days, striatal dopamine had recovered 82% of the level at 3 days. In contrast, DOPAC had only recovered 10.5% in that same period. A similar dynamic was observed in MPTP-lesioned mice pre-treated with the eGFP vector in the present study. Striatal dopamine levels had nearly completely recovered in these mice 35 days following the last MPTP injection, but DOPAC was still significantly lower than in saline-treated mice. DOPAC is formed by the metabolism of dopamine by MAO intracellularly. When dopamine synthesis is compromised, MAO activity is reduced to maintain physiologic levels of dopamine, resulting in lower DOPAC. In contrast to this, DOPAC and dopamine were both normal in MPTP-lesioned mice pre-treated with EpoS71E, despite a lesion size similar to that of mice in the eGFP group.

Densitometric analysis showed a greater density of TH-positive fibers in the striatum of EpoS71E-pretreated mice, suggesting greater sprouting and re-innervation following MPTP lesion. It is well-known that EPO enhances neuronal sprouting and regeneration following in a number of central and peripheral lesion models, including MPTP. Striatal TH-positive fibers in MPTP-lesioned mice pre-treated with EpoR76E did not appear to recover to the extent of those in the EpoS71E group, although the magnitude of difference between saline and MPTP groups was not as great as that in the eGFP controls. This may reflect the smaller lesion size, some moderately-enhanced axonal sprouting, or a combination of the two.

The primary goal of this line of inquiry was to develop an EPO variant that dissociates the erythropoietic effect of EPO from its neuroprotective effect. We show here that a third known effect of EPO, namely its ability to enhance axonal regeneration, is operational in the MPTP lesion model and may be independent of both neuroprotection and erythropoiesis. This may have important treatment implications. There is no cure for Parkinson's disease, and no known intervention that will prevent neurodegeneration. The most common pharmacological interventions replace nigrostriatal dopamine, but the amelioration only lasts a few years and there is some concern that chronic treatment with dopaminergic agonists like L-DOPA may ultimately worsen symptoms. The most common surgical approach is deep-brain stimulation, which involves implantation of a stimulatory electrode in the subthalamic nucleus to dampen the inhibitory tone on nigrostriatal dopaminergic neurons. Unfortunately, it is effective in less than one-third of the patients who undergo surgery. Both of these treatments result in greater stimulation of post-synaptic dopaminergic receptors in the striatum, either through mimicking dopamine or stimulating its endogenous release. However, they do nothing to actively prevent the ongoing neurodegeneration. In contrast, the data presented here indicate that EPO can be administered to protect against further neurodegeneration, as well as to increase sprouting and re-innervation to provide dopamine replacement under conditions of substantial pre-existing nigro-striatal loss.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated nucleic acid molecule encoding a mutant erythropoietin, comprising the nucleic acid sequence set forth as SEQ ID NO: 9.

2. The isolated nucleic acid molecule of claim 1 operably linked to a promoter.

3. An expression vector comprising the isolated nucleic acid molecule of claim 1.

4. The expression vector of claim 3, wherein the expression vector comprises a promoter, wherein the promoter is a cytomegalovirus promoter.

5. The expression vector of claim 3, further encoding a selectable marker.

6. The expression vector of claim 3, wherein the expression vector comprises a mammalian expression vector.

7. The expression vector of claim 6, wherein the mammalian expression vector comprises a viral expression vector.

8. The expression vector of claim 7, wherein the viral expression vector is an adeno-associated virus (AAV) vector.

9. The expression vector of claim 8, wherein the AAV vector is of AAV serotype 1, 2, 3, 4, 5, 6, 7, 8, 9 or a hybrid thereof.

10. An isolated host cell transformed with the nucleic acid molecule of claim 1.

11. A composition comprising the nucleic acid of claim 1 and a pharmaceutically acceptable carrier.

* * * * *